Number: 5,229,410
Date: Jul. 20, 1993

[54] 6-SUBSTITUTED-HEXAHYDROBENZ[C-D]INDOLES

[75] Inventors: Michael E. Flaugh; Michael J. Martinelli, both of Indianapolis; John M. Schaus, Zionsville, all of Ind.

[73] Assignee: Eli Lilly and Company, Indianapolis, Ind.

[21] Appl. No.: 725,177

[22] Filed: Jul. 3, 1991

Related U.S. Application Data

[63] Continuation-in-part of Ser. No. 567,987, Aug. 15, 1990, abandoned.

[51] Int. Cl.$^5$ .................. C07D 209/90; A61K 31/40
[52] U.S. Cl. .................................. 514/411; 548/406; 548/421; 548/436
[58] Field of Search .................. 548/436; 514/411

[56] References Cited

U.S. PATENT DOCUMENTS

| | | | |
|---|---|---|---|
| 2,809,974 | 10/1957 | Kornfeld et al. | 260/326.3 |
| 3,336,307 | 8/1967 | Shen | 268/247.2 |
| 3,671,541 | 6/1972 | Bormann et al. | 260/309.6 |
| 4,057,560 | 11/1977 | Bormann et al. | 260/326.86 |
| 4,110,339 | 8/1978 | Bach et al. | 548/436 |
| 4,576,959 | 3/1986 | Flaugh | 514/411 |
| 4,745,126 | 5/1988 | Leander | 514/411 |
| 4,983,622 | 1/1991 | Flaugh | 514/411 |
| 5,039,820 | 8/1991 | Kress et al. | 548/436 |
| 5,096,908 | 3/1992 | Gidda et al. | 514/307 |

FOREIGN PATENT DOCUMENTS

| | | |
|---|---|---|
| 091328 A2 | 10/1983 | European Pat. Off. |
| 148440 | 12/1984 | European Pat. Off. |
| 0153083 | 8/1985 | European Pat. Off. |
| 162695 A1 | 11/1985 | European Pat. Off. |
| 517732 | 2/1972 | Fed. Rep. of Germany |
| 3525564 A1 | 7/1985 | Fed. Rep. of Germany |

OTHER PUBLICATIONS

Fuller et al, *Advances in Drug Research* 17, pp. 349–380 (1988).
Glennon et al, *J. Med. Chem* 30 pp. 1–12 (1987).
Gonzalez–Heydrich et al, *J. Clin. Psychiatry* 51 pp. 5–12 (1990).
Sayena et al, *J. of Cardiovasc. Pharmacol.* 15 pp. 517–534 (1990).
Dreteler et al., *J. Card. Pharm.*, 14, 770 (1989).
Dreteler et al., *J. Card. Pharm.*, 17, 488 (1991).
Shepheard et al., *Eur. J. Pharm.*, 186, 267 (1990).
Lucot et al., *Pharm. Biochem & Beh.*, 33, 627 (1989).
Othmer et al., *J. Clin. Psych.*, 48(5), 201 (1987).
Bowen et al., *Ann. Neurol.*, 32, 112 (1992).
Bowen et al., *The Lancet* 339, 132 (1992).
Bowen et al., *Trends in Neurosciences* 15, 84 (1992).
Prehn et al., *Eur. J. Pharm.*, 203, 213 (1991).
Dourish et al., *Psychopharmacology*, 86, 197 (1985).
Hutson et al., *Eur. J. Pharm.*, 129, 347 (1986).
Dourish et al., *Psychopharmacology*, 94, 58 (1988).
Dourish et al., *Brain 5-HT$_{1A}$ Receptors: Behavioral and Neurochemical Pharmacology*, Chapter 18, Ellis Harwood, publisher (1987).
Dourish et al., *Brain Res. Bull.*, 15, 377 (1985).
Montgomery et al., *Psychopharmacology*, 94, 110 (1988).
Hutson et al., *Eur. J. Pharm.*, 150, 361 (1988).
Dourish et al., *Appetite 7, Suppl.*, 127 (1986).
Gilbert et al., *Psychopharmacology*, 93, 349 (1987).
Dourish et al., *Psychopharmacology*, 95, 185 (1988).
Neill et al., *Eur. J. Pharm.*, 151, 329 (1988).
Dourish et al., *Brain 5-HT$_{1A}$ Receptors: Behavioral and Neurochemical Pharmacology*, Chapter 20, Ellis Harwood, publisher.
Hilleman et al., *Arch. Intern. Med.*, 152, 350 (1992).
McBride et al., *Pharm. Bio. and Beh.*, 34, 381 (1989).
T. W. Greene, *Protective Groups in Organic Synthesis*, Chapter 7, John Wiley and Sons, New York (1973).
J. W. Barton, *Protective Groups in Organic Synthesis*, Chapter 2, J. F. W. McOmie, ed., Plenum Press, New York, (1973).
*The Vocabulary of Organic Chemistry*, Orchin, et al., John Wiley and Sons, Inc., publishers, p. 126.
A. Schoenberg, et al., *J. Org. Chem.*, 39, 3327 (1974).
A. Schoenberg, et al., *J. Org. Chem.*, 39, 3318 (1974).
Flaugh et al., *J. Med. Chem.*, 31, 1746 (1988).
Nicholas et al., *Org. Prep. and Proc. Int.*, 9, 277 (1977).
Leanna et al., *Tet. Let.*, 30(40), 4946 (1989).
O. Mitsunobu, *Synthesis*, Jan. 1, (1981).
J. P. Freemer et al., *Synthesis*, Dec., 894 (1974).
Y. Sugi, et al., *Bull. Chem. Soc. Jp.*, 43, 1489–1496 (1970).
Morrison and Boyd, Organic Chemistry, Third Edition, Chapter 22, Allyn and Bacon, Boston (1973).
Kornfeld et al., *J.A.C.S.*, 78, 3087 (1956).
Kruse et al., *J. Org. Chem.*, 49, 4761–4768 (1984).
Bach et al., *J. Med. Chem.*, 1980, 23, 481–491.

*Primary Examiner*—Emily Bernhardt
*Attorney, Agent, or Firm*—Douglas J. Taylor; Leroy Whitaker; David E. Boone

[57] ABSTRACT

The present invention provides 4-amino-6-substituted-hexahydrobenz[cd]indoles which are useful in treating disease states which can be benefited by an alteration of 5-HT$_{1A}$ receptors.

22 Claims, No Drawings

6-SUBSTITUTED-HEXAHYDROBENZ[CD]INDOLES

This application is a continuation-in-part of application Ser. No. 07/567,987, filed Aug. 15, 1990, now abandoned.

FIELD OF THE INVENTION

This invention relates to the fields of synthetic organic chemistry and pharmaceutical chemistry and involves hexahydrobenz[cd]indoles which are useful in treating conditions requiring regulation of the serotonin function in the body.

BACKGROUND OF THE INVENTION

Over the last several years it has become apparent that the neurotransmitter serotonin (5-hydroxytryptamine—5-HT) is associated directly or indirectly with a number of physiological phenomena, including appetite, memory, thermoregulation, sleep, sexual behavior, anxiety, depression, blood pressure lowering and hallucinogenic behavior [Glennon, R. A., *J. Med. Chem.*, 30, 1 (1987)].

It has been recognized that there are multiple types of 5-HT receptors. These receptors have been classified as 5-HT$_1$, 5-HT$_2$, and 5-HT$_3$ receptors, with the former being further divided into the subclasses 5-HT$_{1A}$, 5-HT$_{1B}$, 5-HT$_{1C}$, and 5-HT$_{1D}$. The binding affinity of a compound for one or more 5-HT receptors can provide a desirable physiological effect or minimize an undesirable effect. Therefore it is desirable to provide compounds which can bind to 5-HT receptors to act as serotonin agonists or antagonists.

Flaugh in U.S. Pat. No. 4,576,959 (issued 1986) disclosed a family of 6-substituted-4-dialkylamino-1,3,4,5-tetrahydrobenz[cd]indoles which are described as central serotonin agonists. Leander in U.S. Pat. No. 4,745,126 (1988) disclosed a method for treating anxiety in humans employing a 4-substituted-1,3,4,5-tetrahydrobenz[cd]indole-6-carboxamide derivative.

Certain indolines have been reported, as in U.S. Pat. No. 4,110,339 of Bach et al. (1978), Flaugh et al., *J. Med. Chem.*, 31, pp 1746-1753 (1988), Flaugh in U.S. Pat. No. 4,576,959 and European Patent Application 153083 (published 1985). These were used as intermediates in the preparation of the corresponding indoles.

It has now been found that certain 6-substituted-and particularly 6-acyl-substituted-4-aminohexahydrobenz[cd]indoles (indolines) particularly certain stereoisomers of such indolines are useful in treating conditions requiring modification of serotonin function in the body.

SUMMARY OF THE INVENTION

This invention relates to a compound of the Formula I

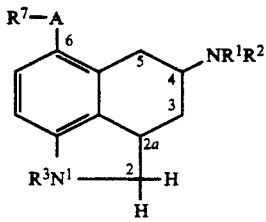

I wherein:
R$^1$ is hydrogen, C$_1$-C$_4$ alkyl, C$_3$-C$_4$ alkenyl, cyclopropylmethyl, phenyl-substituted C$_1$-C$_4$ alkyl, —COR$^4$, —(CH$_2$)$_n$S(C$_1$-C$_4$ alkyl), or —(CH$_2$)$_n$CONR$^5$R$^6$;
R$^2$ is hydrogen, C$_1$-C$_4$ alkyl, C$_3$-C$_4$ alkenyl, or cyclopropylmethyl;
R$^3$ is hydrogen, C$_1$-C$_4$ alkyl or an amino-blocking group;
n is 1-4;
R$^4$ is hydrogen, C$_1$-C$_4$ alkyl, C$_1$-C$_4$ haloalkyl, C$_1$-C$_4$ alkoxy or phenyl;
R$^5$ and R$^6$ are independently hydrogen, a C$_1$-C$_4$ alkyl, or a C$_5$-C$_8$ cycloalkyl;
R$^7$ is C$_1$-C$_8$ alkyl, substituted C$_1$-C$_8$ alkyl, aryl, substituted aryl, aryl (C$_1$-C$_4$ alkyl), substituted aryl (C$_1$-C$_4$ alkyl), C$_3$-C$_7$ cycloalkyl-substituted methyl, or C$_3$-C$_7$ cycloalkyl with the proviso that when A is C≡C then R$^7$ is C$_1$-C$_7$ alkyl, substituted C$_1$-C$_7$ alkyl, aryl, aryl (C$_1$-C$_3$ alkyl), substituted aryl, substituted aryl (C$_1$-C$_3$ alkyl), or C$_3$-C$_7$ cycloalkyl;
A is C=O, CHOH or C≡C; and
pharmaceutically acceptable salts thereof.

In a further embodiment, the instant invention comprises a compound of Formula I wherein
(a) R$^1$, and R$^2$ are independently hydrogen or a C$_1$-C$_4$ alkyl;
(b) R$^3$ is hydrogen;
(c) R$^7$ is C$_1$-C$_8$ alkyl substituted C$_1$-C$_8$ alkyl, phenyl, phenyl (C$_1$-C$_4$ alkyl);
(d) n is 2-4; and
(e) A is C=O; and pharmaceutically acceptable salts thereof.

The invention also provides a pharmaceutical formulation comprising a compound of Formula I and a pharmaceutically acceptable excipient therefor.

A further embodiment of the invention is a method for effecting a biological response at a 5-HT receptor by administering an effective amount of a compound of Formula I. Further embodiments involve the treatment of disease states with require regulation of serotonin function in the body.

DETAILED DESCRIPTION OF THE INVENTION

As used herein, the term "alkyl" represents a straight or branched alkyl chain having the indicated number of carbon atoms. For example, "C$_1$-C$_4$ alkyl" groups are methyl, ethyl, n-propyl, isopropyl, n-butyl, sec.-butyl, isobutyl and tert-butyl. "C$_1$-C$_8$ alkyl" groups include those listed for C$_1$-C$_4$ alkyl as well as n-pentyl, 2-methylbutyl, 3-methylbutyl, n-hexyl, 4-methylpentyl, n-heptyl, 3-ethylpentyl, 2-methylhexyl, 2,3-dimethylpentyl, n-octyl, 3-propylpentyl, 6-methylheptyl, and the like.

The term "C$_3$-C$_4$ alkenyl" refers to olefinically unsaturated alkyl groups such as —CH$_2$CH=CH$_2$, —CH(CH$_3$)CH=CH$_2$, —CH$_2$CH$_2$CH=CH$_2$ and the like.

The term "aryl" means an aromatic carbocyclic structure having one or two rings with a total of six to ten carbon atoms in the rings. Examples of such ring structures are phenyl, naphthyl, indanyl, and the like.

The term "cycloalkyl" means an aliphatic carbocyclic structure having the indicated number of carbon atoms in the ring. For example, the term "C$_3$-C$_7$ cycloalkyl" means cyclopropyl, cyclobutyl, cyclopentyl, cyclohexyl, and cycloheptyl.

The term "aryl ($C_1$–$C_4$ alkyl)" means an aromatic carbocyclic structure joined to a $C_1$–$C_4$ alkyl group. Examples of such groups are benzyl, phenylethyl, α-methylbenzyl, 3-phenylpropyl, α-naphthylmethyl, β-naphthylmethyl, 4-phenylbutyl, and the like. Similarly the term "aryl ($C_1$–$C_3$ alkyl)" means an aromatic carbocyclic structure joined to a $C_1$–$C_3$ alkyl.

The $C_1$–$C_8$ alkyl, the aryl, the aryl ($C_1$–$C_4$ alkyl), and aryl ($C_1$–$C_3$ alkyl) groups can be substituted by one or two moieties. Typical aryl and/or alkyl substituents are $C_1$–$C_3$ alkoxy, halo, hydroxy, $C_1$–$C_3$ thioalkyl, and the like. Moreover, the aryl, aryl ($C_1$–$C_4$ alkyl) and aryl ($C_1$–$C_3$ alkyl) groups can also be substituted by a $C_1$–$C_3$ alkyl or a trifluoromethyl group.

In the foregoing, the term "$C_1$–$C_3$ alkyl" means any of methyl, ethyl, n-propyl, and isopropyl; the term "$C_1$–$C_3$ alkoxy" means any of methoxy, ethoxy, n-propoxy, and isopropoxy; the term "halo" means any of fluoro, chloro, bromo, and iodo; and the term "$C_1$–$C_3$ thioalkyl" means any of methylthio, ethylthio, n-propylthio, and isopropylthio.

Examples of substituted $C_1$–$C_8$ alkyl are methoxymethyl, trifluoromethyl, 6-chlorohexyl, 2-bromopropyl, 2-ethoxy-4-iodobutyl, 3-hydroxypentyl, methylthiomethyl, and the like.

Examples of substituted aryl are p-bromophenyl, m-iodophenyl, p-tolyl, o-hydroxyphenyl, β-(4-hydroxy)naphthyl, p-(methylthio)phenyl, m-trifluoromethylphenyl, 2-chloro-4-methoxyphenyl, α-(5-chloro)naphthyl, and the like.

Examples of the substituted aryl ($C_1$–$C_4$ alkyl) are p-chlorobenzyl, o-methoxybenzyl, m-(methylthio)-α-methyl-benzyl, 3-(4'-trifluoromethylphenyl)propyl, o-iodobenzyl, p-methylbenzyl, and the like.

The term "amino-blocking group" is used as it is frequently used in synthetic organic chemistry, to refer to a group which will prevent an amino group from participating in a reaction carried out on some other functional group of the molecule, but which can be removed from the amine when it is desired to do so. Such groups are discussed by T. W. Greene in chapter 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, which are incorporated herein by reference in their entirety. Examples of such groups include those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl, benzyl and substituted benzyl such as 3,4-dimethoxybenzyl, o-nitrobenzyl, and triphenylmethyl trityl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred amino blocking groups are benzyl (—$CH_2C_6H_5$), trityl, acyl [C(O)R] or $SiR_3$ where R is $C_1$–$C_4$ alkyl, halomethyl, 2-halo-substituted alkoxy, or phenyl.

The compounds of the instant invention have at least 2 chiral centers and therefore at least four stereoisomers can exist for each. Chiral centers exist at position 2a and 4 as in Formula I. If a substituent group contains a chiral center, then additional stereoisomers can of course exist. Racemic mixtures as well as the substantially pure stereoisomers of Formula I are contemplated as within the scope of the present invention. The term "substantially pure" refers to at least about 90 mole percent, more preferably at least about 95 mole percent, most preferably at least about 98 mole percent of the desired stereoisomer being present compard to the other stereoisomers present. Particularly preferred stereoisomers of Formula I are those in which the configuration of the chiral center at position 2a is S and at position 4 is R, i.e., 2aS, 4R.

The terms "R" and "S" are used herein as commonly used in organic chemistry to denote specific configuration of chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereo chemistry is contained in the book: *The Vocabulary of Organic Chemistry*, Orchin, et al. John Wiley and Sons Inc., publishers, page 126, which is incorporated herein by reference.

While all of the compounds of the invention are useful for the purposes taught herein, certain of the present compounds are preferred for such uses. Preferably $R_1$ and $R_2$ are both $C_1$–$C_4$ alkyl, and especially n-propyl. $R^3$ is preferably hydrogen, $R^7$ is preferably $C_1$–$C_4$ alkyl, substituted $C_1$–$C_4$ alkyl, or $C_3$–$C_7$ cycloalkyl. Although compounds in which A is CHOH or C≡C have activity, their primary utility is as intermediates in the preparation of compounds in which A is C=O. Other preferred aspects of the present invention are noted hereinafter.

As pointed out above, this invention includes the pharmaceutically-acceptable salts of the compounds of Formula I. Since the compounds of this invention are amines, they are basic in nature and accordingly react with any number of inorganic and organic acids to form pharmaceutically acceptable salts such as hydrochloric acid, nitric acid, phosphoric acid, sulfuric acid, hydrobromic acid, hydroiodic acid, phosphorous acid and others, as well as salts derived from non-toxic organic acids such as aliphatic mono and dicarboxylic acids, amino acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate isobutyrate, caprate, heptanoate, propiolate, oxalate, malonate, succinate, suberate, sebacate, fumarate, maleate, mandelate, butyne-1,4-dioate, hexyne-1,6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, b-hydroxybutyrate, glycolate, malate, naphthalene-1-sulfonate, naphthalene-2-sulfonate and mesylate.

The following list illustrates representative compounds of the present invention:
4-(di-n-propylamino)-6-acetyl-1,2,2a,3,4,5-hexahydrobenz[cd]indole;
4-(di-n-propylamino)-6-(2,2-dimethylpropanoyl)-1,2,2a,3,4,5-hexahydrobenz[cd]indole;
4-(diethylamino)-6-propanoyl-1,2,2a,3,4,5-hexahydrobenz[cd]indole;
4-(di-n-propylamino)-6-benzoyl-1,2,2a,3,4,5-hexahydrobenz[cd]indole;
(2aS,4R)-4-(n-propylamino)-6-(2-methylpropanoyl)-1,2,2a,3,4,5-hexahydrobenz[cd]indole;
1-methyl-4-(di-n-propylamino)-6-benzoyl-1,2,2a,3,4,5-hexahydrobenz[cd]indole;
1-methyl-4-(n-propylamino)-6-(3-methylbutanoyl)-1,2,2a,3,4,5-hexahydrobenz[cd]indole;
(2aS,4R)-4-(di-n-propylamino)-6-(2,2-dimethylpropanoyl)-1,2,2a,3,4,5-hexahydrobenz[cd]indole;
(2aS,4R)-4-(di-n-propylamino)-6-benzoyl-1,2,2a,3,4,5-hexahydrobenz[cd]indole; and
4-(N-n-propyl-N-cyclopropylmethyl)amino-6-propanoyl-1,2,2a,3,4,5-hexahydrobenz[cd]indole;
(2aS,4S)-4-(di-n-propylamino)-6-acetyl-1,2,2a,3,4,5-hexahydrobenz[cd]indole;
(2aS,4R)-4-(di-n-propylamino)-6-(2-phenylethanoyl)-1,2,2a,3,4,5-hexahydrobenz[cd]indole; and Scheme 1 depicts a process for preparing compounds of the present invention wherein $R^1$, $R^2$ and $R^7$ are as defined above and Z is an amino-blocking group as defined hereinabove.

According to one route of this process, a 4-amino-6-bromohexahydrobenz[cd]indole 1 is combined with an equimolar to slight excess amount of potassium hydride in diethyl ether. The reagents are generally combined at a cold temperature, typically in the range of about −20° C. to about 10° C., preferably at about 0° C. The resulting mixture is cooled to a temperature in the range of about −100° C. to about −60° C., preferably at about −78° C., and combined with a lithiating reagent, preferably in at least a two molar excess amount. Suitable lithiating reagents include sec-butyllithium, the preferred t-butyllithium, and other similar organolithium compounds is preferred. The reaction is preferably conducted at a temperature in the range of about −100° C. to about −20° C., more preferably at about −60° C. to about −40° C.

The 4-amino-6-lithiohexahydrobenz[cd]indole 2 thus prepared is then contacted with an appropriate electrophile such as L-C(O)$R^7$ wherein $R^7$ is defined above and L is a good leaving group such as chlorine bromine, methoxy, phenoxy and the like. Typically, a solution of the compound 2 at a temperature in the range of about −100° C. to about −60° C., preferably at about −80° C., is added to a solution of this reagent in a mutual solvent. If an excess amount of the electrophile is employed in the reaction, the 1-amino group will also be acylated (i.e. Z is the acyl group $R^7C(O)$ in compound 3a) and a subsequent hydrolysis reaction is required to provide the free indoline, I. A 1:1 ratio of electrophile to lithiated indoline (compound 2) can be used to minimize acylation of the 1-nitrogen. The reaction is preferably conducted at a temperature in the range of about −40° C. to about 10° C. The desired compound is purified by quenching the reaction mixture with, for example, ice water when a 1:1 ratio is used. With a higher ratio in which significant 1-acylation is obtained, the product is hydrolyzed using an acid such as sulfuric acid or a base such as sodium hydroxide. The mixture is then washed with a water-immiscible organic solvent. The organic phase is extracted with acid; the aqueous phases are combined and made basic; and the desired compound is extracted with a water immiscible organic solvent. The organic solvent is then concentrated, typically under vacuum, and the desired compound I is further purified, if necessary, by standard procedures.

In an alternative route, the 1-nitrogen can be "blocked" or "protected" before initiating the metallation reaction. A blocking group (depicted as "Z" such as $SiR_3$, C(O)R, or $CH_2(C_6H_5)$ where R is $C_3$–$C_4$ alkyl or phenyl $(C_6H_5)$ is preferably used to provide compound 1a. Compound 1a is then reacted with a lithiating agent as described above to provide compound 2a. Compound 2a can then be acylated by contacting with a suitable electrophile as described hereinabove. The resulting compound 3a is then deprotected by hydrolysis when Z is $SiR_3$. When Z is benzyl, compound 3a can be subjected to hydrogenolysis over a catalyst such as palladium to remove the benzyl group. The desired compound is isolated by standard conditions and purified by crystallization from common solvents or column chromatography over solid supports such as silica gel or alumina.

An alternative synthesis of the compounds I is depicted in Scheme 2 and involves treatment of the 6-lithio derivatives 2 and 2a (depicted in Scheme 1) with an aldehyde, $R^7CHO$, to form an alcohol 4 or 4a. Oxidation of the alcohol can be accomplished with oxidants known to those skilled in the art for such purposes such as pyridinium chlorochromate, dimethylsulfoxide and oxalyl chloride, an aqueous solution of chromic acid and sulfuric acid, and the like. Deprotection of the 1-amino group provides the free amine compounds I.

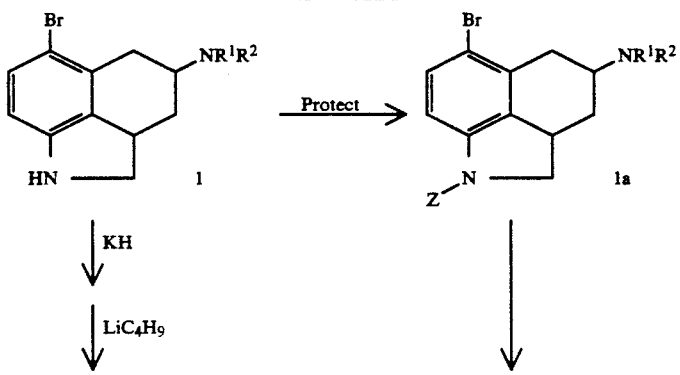

Scheme 1

Scheme 1
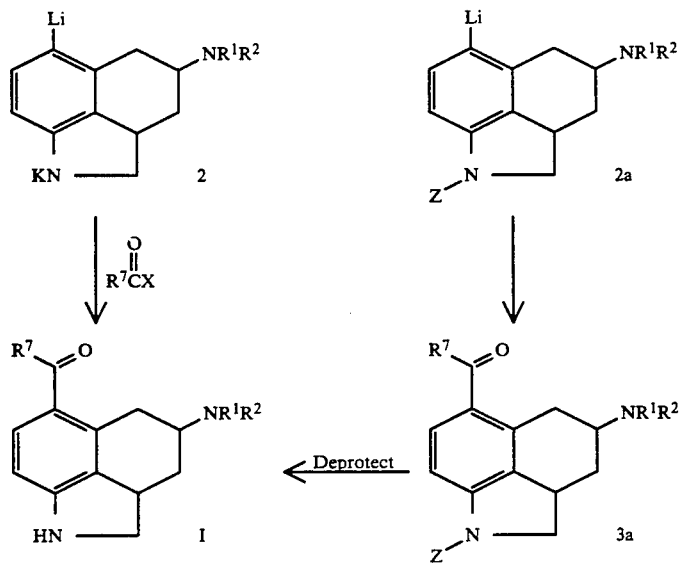
Scheme 2
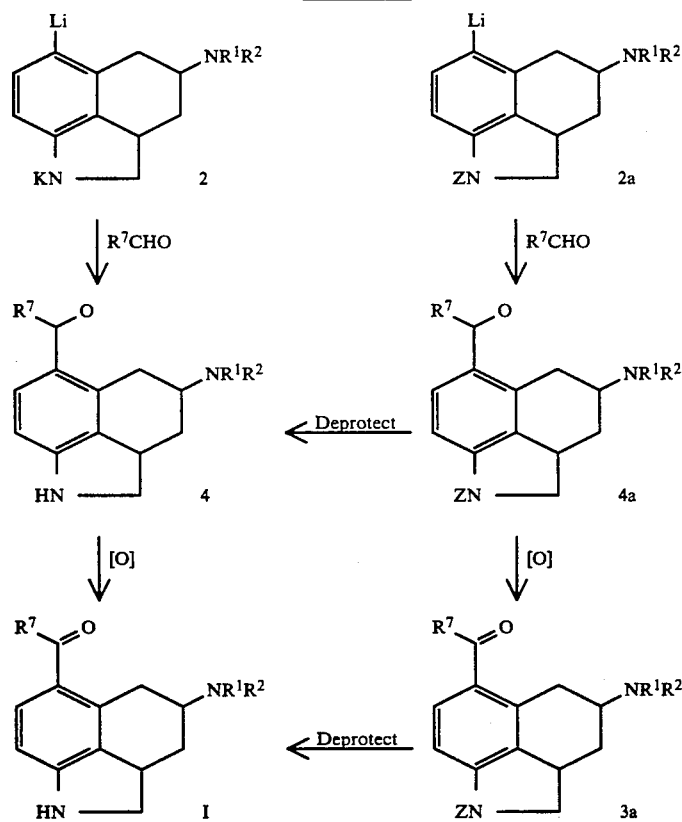
The alcohol intermediates 4 and 4a can alternatively be prepared as depicted in Scheme 3 by addition of an organometallic reagent (R⁷M) such as an alkyl lithium R⁷Li or a Grignard reagent R⁷MgX to aldehyde 5 and 5a, respectively.

Scheme 3

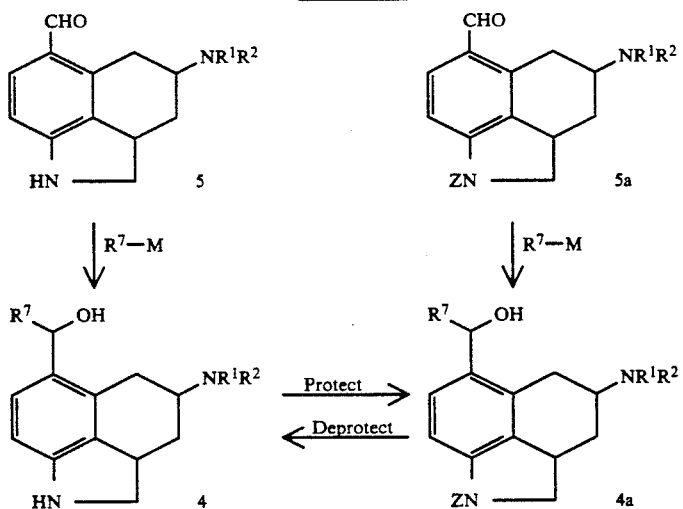

Various routes can be used to prepare aldehydes 5 and 5a. The methods disclosed herein are not intended to be exhaustive and other procedures may be apparent to those skilled in the art. One route involves treating 6-lithioderivatives 2 and 2a with dimethylformamide followed by aqueous work up. Another method depicted in Scheme 4 involves the preparation of the 6-nitrile derivative 6 followed by partial reduction and hydrolysis.

Scheme 4

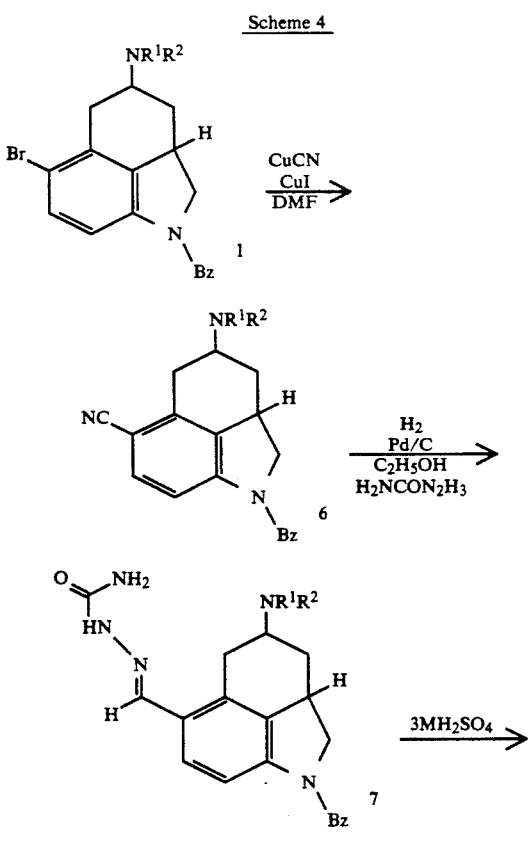

-continued
Scheme 4

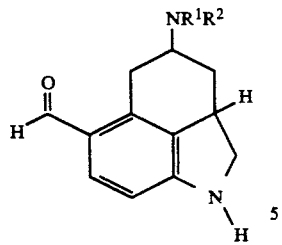

The 1-benzoyl-6-bromo-derivative 1 is contacted with a mixture of cuprous cyanide and cuprous iodide in dimethylformamide at about 140° C. The resulting 6-nitrile 6 is hydrogenated over Pd/C in the presence of semicarbazide to provide the 6-semicarbazone, compound 7. This is hydrolyzed using sulfuric acid to provide aldehyde 5.

In an alternative method of preparation, depicted in Scheme 5, the 6-nitrile derivative 6 is contacted with a reducing agent [H] such as diisobutylaluminum hydride. The resulting aldehyde 5a can be contacted with an organometallic reagent such as a Grignard reagent, $R^7MgBr$, to provide alcohol 4a which is oxidized as described hereinabove to the 1-blocked-6-acyl derivative 3a.

Scheme 5

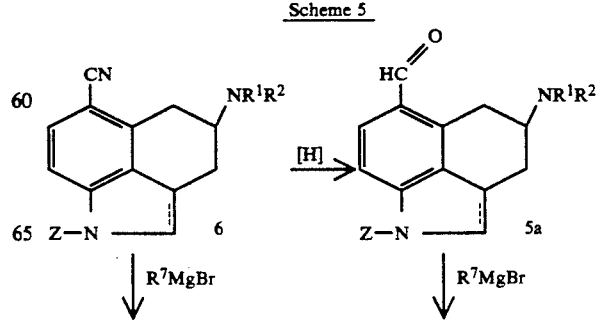

-continued
Scheme 5

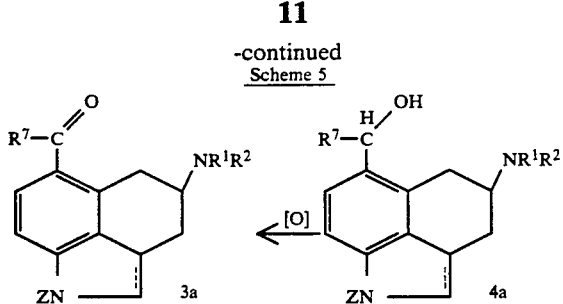

Another method of preparation of compounds of Formula I involves the Friedel-Crafts acylation of the 6-H indoline 8 as depicted in Scheme 6. The indoline 8, wherein $R^1$, $R^2$ and Z are as defined hereinabove, is contacted with an acylating agent such is the benzoyl group. The blocking group can be removed from compound 3a by hydrolysis, preferably using a base such as sodium hydroxide, to provide compound I.

Alternatively, certain compounds of Formula I can be prepared using the 6-iodo derivative 9 as depicted in Schemes 7 and 8 wherein $R^1$, $R^2$ and Z are as defined hereinabove. In Scheme 7 a method is shown in which a 6-alkyne derivative is prepared. This method provides 6-acyl compounds in which there is a methylene group adjacent to the carbonyl group. In this method the 1-amino group is protected with a group (represented by Z) such as a benzoyl group. This compound 9 is contacted with a palladium catalyst $Pd(PPh_3)_4$ [where Ph is phenyl] and the tin alkyne compound $R^{7a}$—C≡C—$Sn(CH_3)_3$. $R^{7a}$ is a $C_1$-$C_7$ alkyl, substituted $C_1$-$C_7$ alkyl, aryl, aryl ($C_1$-$C_3$ alkyl), substituted aryl, substi- Scheme 6

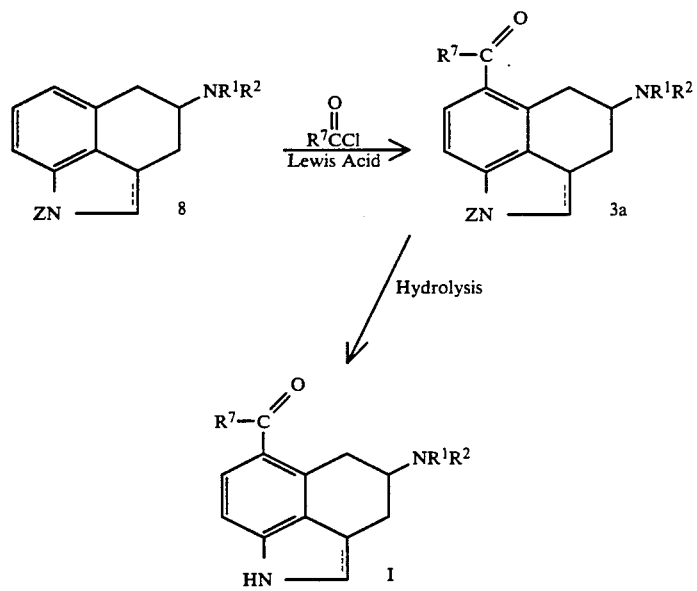

as a carboxylic acid anhydride [$(R^7CO)_2O$] or a carboxylic acid halide, particularly the acid chloride $R^7C(O)Cl$, in the presence of a Lewis Acid. Preferred Lewis Acids include aluminum chloride, aluminum bromide, $BF_3$, $SnCl_4$, HF, $TiCl_4$, and the like. The reaction is preferably conducted in a solvent commonly used for such acylation reactions, such as nitrobenzene, and the like. The reaction is normally conducted at a temperature in the range of 20° C. to reflux. Preferably the 1-amino group is protected with a blocking group depicted as Z in Scheme 6. A preferred blocking group tuted aryl ($C_1$-$C_3$ alkyl), or $C_3$-$C_7$ cycloalkyl group. This reaction is normally conducted in a solvent such as toluene at an elevated temperature, e.g. about 100° C. Typically an excess of the tin alkyne is used along about 0.25 equivalents of the palladium compound based on compound 9. The 6-alkyne 10 is then contacted with $HgSO_4$ in water or with aqueous acid to provide the ketone 11. The 1-blocking group can be removed by hydrolysis with base as described above to provide compound I.

Scheme 7

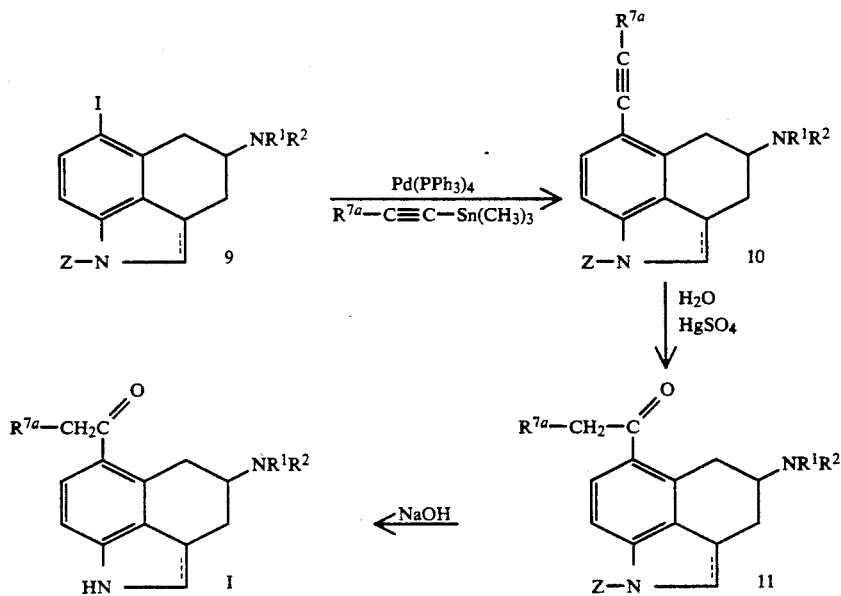

In Scheme 8 a preparative method is depicted in which a vinyl ether is reacted with the 6-iodo derivative 9. $R^1$, $R^2$ and Z are as defined hereinabove with Z preferably a benzoyl group, except as provided below. This method provides a 6-(1-alkoxyalkenyl) derivative 81 which can then be hydrolyzed and deprotected to provide the desired compound of Formula I. Alternatively, the derivative 81 can be deprotected, with for example butyl lithium, and then the vinyl group hydrolyzed. In this method the 1-amino group is protected with an amino protecting group, preferably a benzoyl group. This compound 9 is then contacted with a palladium catalyst and the desired vinyl ether. The vinyl ethers useful in this method include those in which $R^c$ is a $C_1$-$C_4$ alkyl and Q is hydrogen or an alkyl tin, alkyl or alkoxy boron, zinc halide, or magnesium halide, for example tributyltin. When Q is zinc halide or magnesium halide, it is preferred that Z be a group such as trityl. $R^a$ and $R^b$ can independently be hydrogen, $C_1$-$C_6$ alkyl, substituted $C_1$-$C_6$ alkyl, aryl, aryl ($C_1$-$C_2$) alkyl, substituted aryl, substituted aryl ($C_1$-$C_2$) alkyl, or $C_3$-$C_7$ cycloalkyl group. The palladium catalyst used can be palladium powder (black) or Pd(PPh$_3$)$_4$ [where Ph is phenyl]. The Pd(PPh$_3$)$_4$ is commonly used with toluene at reflux. The Pd-black can be used with triphenylphosphine in toluene at reflux or in a mixture of acetonitrile and triethyl amine at about 100° C. Similar reactions are reported in *Bull. Chem. Soc. Jpn.* (1987), 60, 767-768, incorporated herein by reference.

Scheme 8

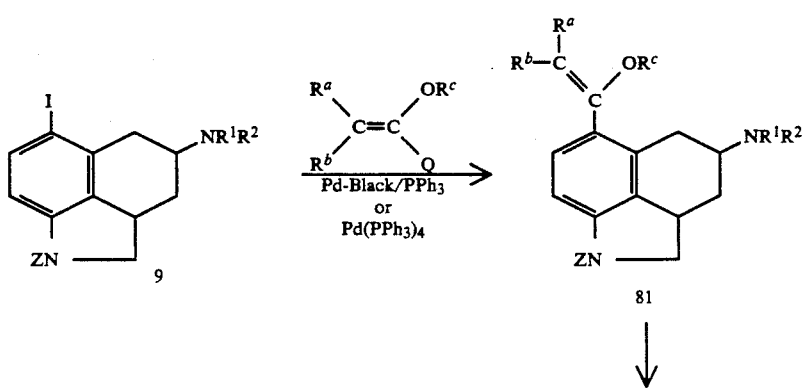

Scheme 8

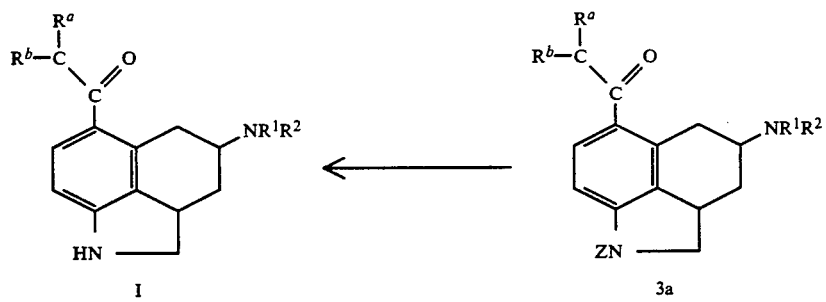

In another preparation method depicted in Scheme 9, the 6-iodo derivative 9 can be used to prepare certain 6-acyl compounds directly. This is accomplished by contacting the 6-iodo compound with trialkyltin-alkyl complex and carbon monoxide in the presence of a palladium catalyst Pd(PPh$_3$)$_4$ [where Ph is phenyl] as described in the literature for arylhalides. [A. Schoenberg and R. F. Heck, *J. Org. Chem.*, 39, p. 3327 (1974); and A. Schoenberg, I. Bartoletti, and R. F. Heck, *J. Org. Chem.*, 39, p. 3318 (1974)]. The blocking group Z which is preferably benzoyl for this method can be removed as described hereinabove to provide compound I.

Scheme 9

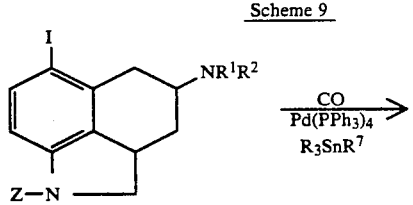

-continued
Scheme 9

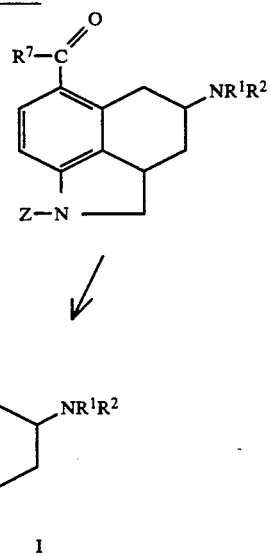

The processes depicted in Schemes 1-9 can result in a mixture of products which require purification by standard methods of purfication, for example, crystallization or chromatographic techniques as appropriate.

Scheme 10 illustrates a preparation of the starting material for reaction Scheme 1.

Scheme 10

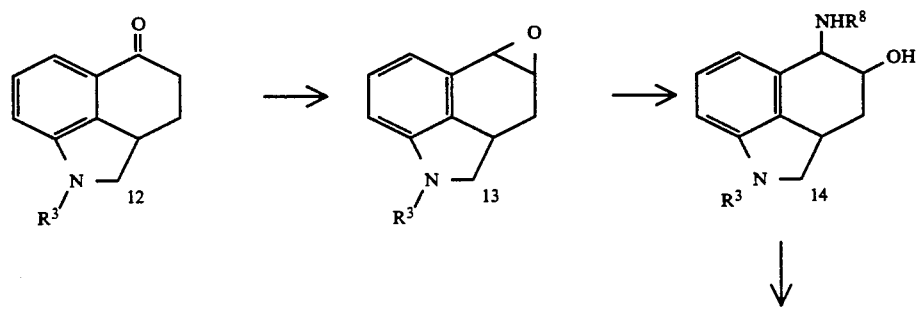

Scheme 10

-continued

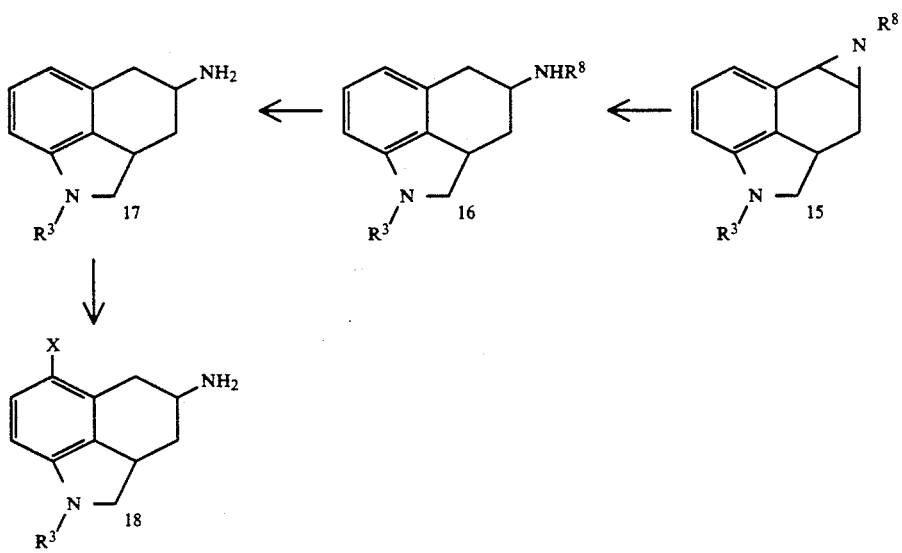

Epoxides of formula 13 are known in the art or can be prepared from compounds such as ketone 12, which is known to the art, using common reagents and techniques. For example, Flaugh, et al., *J. Med. Chem.*, 31, 1746 (1988); Nichols et al., *Org. Prep. and Proc., Int.*, 9, 277 (1977); and Leanna et al., *Tet. Lett.*, 30, No. 30, 3935 (1989), teach methods of preparation of various embodiments of compounds of formula 13. Those skilled in the art of organic chemistry will recognize that there are four stereoisomers of formula 13:

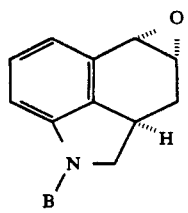 13a

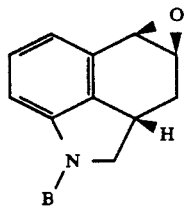 13b

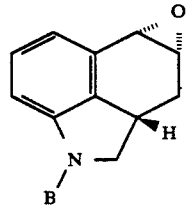 13c

-continued

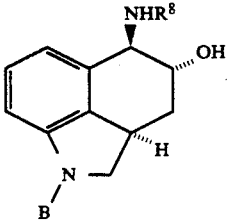 13d

Formulae 13a and 13b are herein referred to collectively as the exo-isomers; similarly, formulae 13c and 13d are the endo-isomers. Leanna et al., supra, teach the preparation of epoxides of formula 13 which are substantially exo or substantially endo, as desired. A preferred starting material is the compound of formula 13 wherein $R^3$ is benzoyl; the most preferred starting material is the mixture of substantially the exo-isomers thereof.

Amino alcohols of formula 14 are formed by reacting an epoxide of formula 13 with an amine of formula $R^8NH_2$, where $R^8$ can be hydrogen, a $C_1$-$C_4$ alkyl, or a $C_1$-$C_4$ alkyl substituted with one to three groups selected from halogen, nitro or phenyl. Such amines are readily available. Opening of the epoxide ring proceeds substantially regiospecifically with the amino group at the 5-position and the hydroxyl group at the 4-position. The reaction is also stereospecific in the sense that stereoisomers of formulae 14a-d are predictably formed from, respectively, stereoisomers of formulae 13a-d.

14a

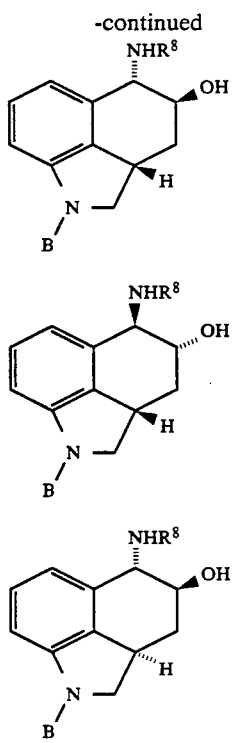

A stereoselective synthesis of the amino alcohol of formula 14, and hence of all the subsequent intermediates and products of Scheme 10, can be effected by using a substantially pure enantiomer of an amine of the formula $R^8NH_2$, wherein $R^8$ contains at least one chiral center. A particularly preferred amine is (+) or (−) 1-phenylethylamine. The diastereomers of the resulting amino alcohol can then be separated by a number of means known in the art, for example by chromatography or crystallization. Suitable solvents for recrystallization include those such as diethyl ether, butanol, and mixtures of hexane and ethyl acetate. An alternative method of achieving a stereospecific synthesis comprises conversion of all the diastereomers of formula 14 to corresponding diastereomers of formula 15, followed by the separation of said diastereomers of formula 15; that alternative method is discussed below. If a stereoselective synthesis is not desired, then separation of the stereoisomers of the amino alcohol of formula 13 is not required and the amine $R^8NH_2$ need not be optically active.

A particularly efficient stereoselective process for a highly preferred compound of formula 14, 1-benzoyl-4-hydroxy-5-(1-phenylethyl)amino-1,2,2a,3,4,5-hexahydrobenz[cd]indole, comprises the reaction of a mixture of substantially the exo-isomers of the corresponding epoxide of formula 13, or a mixture of substantially the endo-isomers of the corresponding epoxide of formula 13, with a substantially pure enantiomer of 1-phenethylamine in the solvent butanol and the subsequent selective crystallization of one of the two isomers of the amino alcohol. The temperature of the reaction is preferably from about 50° to about 150° C., more preferably in the range of about 80° to about 100° C.

After the reaction is complete, as determined for example by thin layer chromatography or liquid chromatography, the desired amino alcohol is crystallized at about −20° to about 40° C.; the preferred temperature for the crystallization is about 0° to about 15° C. Therefore this process has the valuable attribute that the reaction and the separation of stereoisomers occur efficiently in a single step. By the proper selection of the epoxide isomers, exo or endo, and the enantiomer of 1-phenylethylamine, R or S, one can determine which of the stereoisomers of the compound of formula 14 precipitates from the reaction mixture. For example, a preferred stereoisomer of 1-benzoyl-4-hydroxy-5-(1-phenylethyl)amino-1,2,2a,3,4,5-hexahydrobenz[cd]indole, the (2a-S,4-R,5-R)-isomer can be selectively prepared by reacting the exo-epoxides with S-1-phenylethylamine.

A number of methods of forming aziridines such as those of formula 15 from amino alcohols such as those of formula 14 are known to the art. Two examples are the use of diethyl azodicarboxylate and triphenylphosphine (O. Mitsunobu, *Synthesis*, January, 1981, page 1), and the use of bromine and triphenylphosphine (J. P. Freemer and P. J. Mondron, *Synthesis*, December, 1974, page 894).

A particularly efficient alternative to the above methods involving treating a compound of formula 14 with a tertiary amine in an inert solvent followed by the addition of methanesulfonyl chloride. The stereoisomers 15a–d of the aziridine 15 arise respectively from the stereoisomers of formula 14a–d with retention of configuration at any chiral center in the substituents $R^3$ or $R^8$ as well as at position 2a:

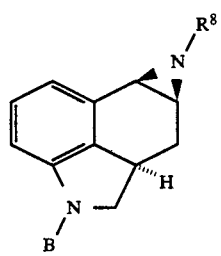

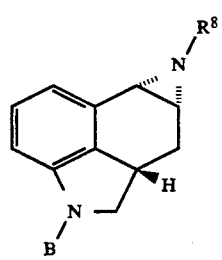

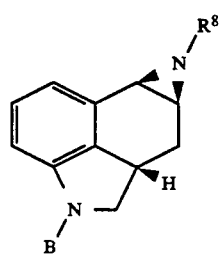

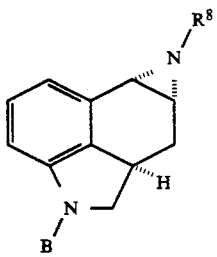

15d

Suitable tertiary amines include those of the formula $(R^9)_3N$, where the $R^9$ groups are independently $C_1$–$C_4$ alkyl. Suitable solvents are chlorinated hydrocarbons such as methylene chloride, chloroform, carbon tetrachloride, and dichloroethane; aromatic hydrocarbons such as benzene, toluene, and the xylenes; and ethers such as tetrahydrofuran, diethyl ether, and methyl t-butyl ether. The reaction can be conducted at a temperature from about −35° to about 45° C. In the preferred embodiment, the amino alcohol is treated with triethylamine in methylene chloride at about −20° to about 0° C., then the reaction mixture is warmed to about 15° to about 35° C. for the completion of the reaction. If desired, the product, an aziridine of formula 15, can be crystallized from an appropriate solvent such as acetonitrile or isopropanol after an aqueous workup. In the event that $R^8$ contains at least one chiral center in substantially a single stereoconfiguration, the individual stereoisomers of the aziridine of formula 15 can be separated by methods such as chromatography and crystallization, thereby providing a stereospecific synthesis of the aziridine of formula 15 and subsequent products.

The aziridine ring can be opened to form an intermediate secondary amine of formula 16. A number of methods of opening aziridines are commonly known. It is, however, crucial that the method used for opening the aziridine to form a secondary amine of formula 16 be substantially regiospecific, i.e., the aziridine must be opened to form substantially the 4-amino compound rather than the 5-amino compound. One such method is catalytic hydrogenolysis as taught by Y. Sugi and S. Mitsui, *Bull. Chem. Soc. Jap.*, 43, pp. 1489–1496 (1970). Catalysts which are suitable are the usual hydrogenation and hydrogenolysis catalysts, such as the noble metal catalysts; the preferred catalyst is palladium. Suitable solvents include hydrocarbons such as hexanes and heptanes; aromatic hydrocarbons such as benzene, toluene, xylenes, ethylbenzene, and t-butylbenzene; alcohols such as methanol, ethanol, and isopropanol; and mixtures of solvents such as acetic acid mixed with said alcohols. Preferred solvents for preparing the compound of formula 16, wherein $R^3$ is benzoyl, and $R^8$ is 1-phenylethyl, include glacial acetic acid or a mixture of methanol and phosphoric acid. The source of hydrogen can be an atmosphere of elemental hydrogen supplied at a pressure of about 1 atmosphere or higher, or the source of hydrogen can be compounds which are suitable to serve as hydrogen donors in a catalytic transfer hydrogenolysis reaction, such as formic acid, cyclohexene or hydrazine. The preferred hydrogen source is an atmosphere of hydrogen gas supplied at about 1 to about 10 atmospheres pressure. The temperature of the reaction may be from about −20° to about 80° C.; the preferred temperature for the hydrogenolysis of the aziridine wherein $R^3$ is benzoyl and $R^8$ is 1-phenylethyl is about −20° to about 0° C.

The conversion of compounds of formula 15 to compounds of formula 16 proceeds without disturbing the stereochemical configuration of the chiral centers at the 2a- or 4-positions of the formula 16 or of the chiral centers that may be present in any of the substituents.

If desired, the compound of formula 16 can be isolated by the usual methods such as crystallization. The secondary amine at position 4 of formula 16 can be converted to a primary amine of formula 17 by a number of methods known to the art of organic chemistry, or alternatively the secondary amine itself can be isolated. However, a preferred method is to convert the secondary amine of formula 16 to the primary amine of formula 17 without isolating the secondary amine, but rather by simply continuing without interruption the hydrogenolysis reaction that produced the compound of formula 16. Therefore, the preferred solvent and catalyst are the same as those for the preparation of the secondary amine of formula 16. It may be desirable to conduct the hydrogenolysis of the secondary amine of formula 16 at a different temperature or a different pressure or different temperature and pressure than the hydrogenolysis of the aziridine of formula 15. For the hydrogenolysis of the preferred compound of formula 16 wherein $R^3$ is benzoyl and $R^8$ is 1-phenylethyl, the preferred temperature and pressure are about 50° to about 60° C. and about 1 to about 20 atmospheres. Under these conditions, the hydrogenolysis of compounds of formula 16 to compounds of formula 17 proceeds without disturbing the stereochemical configuration of the chiral center at the 4-position.

The isolation of the compound of formula 17 can be accomplished by the usual methods such as crystallization. If desired, the compound of formula 17 can be further purified, for example by recrystallization.

The compound of formula 17 can be halogenated to provide, for example, the 6-bromo or 6-iodo derivative 18. Iodination of compound 17 can be accomplished by using iodine and orthoperiodic acid in the presence of an acid such as sulfuric acid or trifluoroactic acid, in a solvent such as acetic acid. Another method of iodination involves the use of N-iodosuccinimide in the presence of trifluoroacetic acid. The 6-bromo derivative can be prepared using bromine in acetic acid or using N-bromosuccinimide.

Of course, as those skilled in the art will recognize, variations of any of the Schemes discussed herein may be desirable or necessary for certain embodiments of the invention. Such variations are contemplated as within the scope of the present invention.

Compounds of Formula I can be prepared from the appropriate compound of formula 18, whether it exists as a mixture of stereoisomers or as a substantially pure diastereomer using common reagents and methods well known in the art. A preferred intermediate to the compounds of the instant invention is the 6-bromoderivative of 18 although the 6-iodo derivative is preferred if the carbonylation reaction of Scheme 8 is used. Preferably $R^3$ is an amino-blocking group such as benzoyl. Amino blocking groups can be added, if desired, to the 4-amino substituent using such methods as those disclosed by Greene, supra, and Barton, supra. Alkyl groups can be added, if desired, to the 4-amino substituent using such common methods as reaction of the 4-amine with the appropriate halide as discussed by Morrison and Boyd, Chapter 22, *Organic Chemistry*, Third Edition, Allyn and Bacon, Boston, 1973. If desired, the benzoyl group can be removed from the 1-position using known methods and optionally replaced with other amino-protecting groups. The amino-protecting groups and alkyl groups can be added either before or after the bromination, as desired.

The 4-amino-6-bromohexahydrobenz[cd]indole starting materials used to prepare the compounds of the invention can be readily prepared by other processes such as disclosed in U.S. Pat. No. 4,576,959 and EPO Application 153083 of Flaugh, each of which is incorporated herein by reference in its entirety.

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designed, for example, "°C" refers to degrees celsius; "N" refers to normal or normality; "mmol" referes to millimole; "g" referes to gram; "ml" means milliliter; "M" refers to molar; "min" refers to minutes; "hr" refers to hours; "EtOAc" refers to ethyl acetate; "RT" refers to room temperature; "sat'd" means saturated; "ppt" means precipitate; "Et$_2$O" refers to ethyl ether; "THF" refers to tetrahydrofuran; "MsCl" refers to mesyl chloride; "NMR" refers to nuclear magnetic resonance; "IR" refers to infrared spectroscopy; "U.V." refers to ultraviolet spectroscopy; and "m.s." refers to mass spectrometry.

EXAMPLE 1

Preparation of mixture of (2aS,4R)-, (2aR,4S)-1-Benzoyl-6-cyano-4-(di-n-propylamino)-1,2,2a,3,4,5-hexahydrobenz[cd]indole.

To a solution of dimethyl formamide (100 mL) containing a mixture of (2aS,4R)- and (2aR,4S)-1-benzoyl-6-bromo-4-(di-n-propyl-amino)hexahydrobenz[cd]indole under a N$_2$ atmosphere were added 3.4 g (37.5 mmol) of CuCN and 7.1 (37.5 mmol) of CuI. The reaction mixture was then stirred at 140° C. for 6 hours. The reaction mixture was poured onto ice, diluted with water, CH$_2$Cl$_2$ was added and the mixture stirred for 30 minutes. The mixture was filtered through a diatomaceous earth (tradename "Celite") pad and the filtrate was extracted twice with CH$_2$Cl$_2$. The organic solution was dried over MgSO$_4$ and then evaporated to provide 4 g of solid. Chromatography of this crude product over silica gel with 1:19 MeOH/CH$_2$Cl$_2$Cl$_2$ as eluent gave 3 g (62%) of product.

EXAMPLE 2

Preparation of mixture of (2aS,4R)-, (2aR,4S)-6-cyano-4-(di-n-propylamino)-1,2,2a,3,4,5-hexahydrobenz[cd]indole.

To a stirred solution of 4.8 g (0.0124 mol) of 1-benzoyl-6-cyano-4-(di-n-propylamino)-1,2,2a,3,4,5-hexahydrobenz[cd]indole prepared as in Example 1 in 200 mL of THF cooled to −78° C. under N$_2$ atmosphere, was added 16 mL (0.025 mol) of 1.6M solution of n-butyllithium in hexane. The reaction mixture was stirred at −78° C. for 30 minutes and then allowed to warm to −20° C. To the reaction mixture was added 100 mL in 1N HCl. The mixture was extracted once with ethyl ether. The acidic solution was made alkaline with the addition of cold 5N NaOH. The basic mixture was extracted twice with CH$_2$Cl$_2$. The combined organic solution was washed with saturated aqueous NaCl solution. The CH$_2$Cl$_2$ solution was dried over MgSO$_4$ and evaporated to give 4 g of an oil. Chromatography of this oil over silica gel with ethyl acetate as eluent gave 3 g (85%) of product as an oil, which upon standing solidified.

EXAMPLE 3

Preparation of mixture of (2aS,4R)-, (2aR,4S)-6-acetyl-4-(di-n-propylamino)-1,2,2a,3,4,5-hexahydrobenz[cd]indole.

A solution of 0.5 g (1.8 mmol) of 6-cyano-4-(di-n-propylamino)-1,2,2a,3,4,5-hexahydrobenz[cd]indole prepared as in Example 2 in 75 mL of benzene was treated with 5 mL of 2.0M methylmagnesium bromide in diethyl ether. The reaction mixture was refluxed for 2 days. The reaction mixture was cooled and excess Grignard reagent was decomposed with addition of saturated aqueous NH$_4$Cl solution. The benzene layer was separated and washed once with saturated aqueous NaCl solution. The organic solution was evaporated to an oil. The oil was dissolved in 25 mL of 5N HCl and the solution was stirred at room temperature for 30 minutes. The acidic solution was made alkaline with the addition of excess concentrated aqueous NH$_4$OH solution. The basic mixture was extracted twice with CH$_2$Cl$_2$. The combined organic solution was washed once with saturated aqueous NaCl solution and dried over MgSO$_4$. The CH$_2$Cl$_2$ solution was evaporated to yield 0.5 g of an oil. Chromatography of this oil over silica gel with ethyl acetate as eluent gave 0.4 g (75%) of product as an oil, which upon standing solidified, m.p. 76°–77° C.

Analysis for (C$_{19}$H$_{28}$N$_2$O): Theory: C, 75.96; H, 9.39; N, 9.32. Found: C, 75.66; H, 9.33; N, 9.38.

NMR: (300 MHz, CDCl$_3$) d 0.89 (t, 6H, CCH$_3$), 1.46 (mult, 5H, 3α-H and CH$_2$Me), 2.16 (br d, 1H, 3β-H), 2.49 (mult, 4H, CH$_2$Et), 2.50 (s, 3H, COCH$_3$), 2.87 (dd, 1H, 5α-H), 3.15 (mult, 1H, 2α-h), 3.19 (mult, 2H, 2α-H and 2β-H), 3.42 (dd, 1H, 5β-H), 3.73 (mult, 1H, 4-H), 4.04 (br s, 1H, 1-H), 6.43 (d, 1H, 8-H), 7.63 (d, 1H, 7-H).

M.S.: m/e=300 (fd).

EXAMPLE 4

Preparation of (2aR,4R)-6-acetyl-4-(di-n-propylamino)-1,2,2a,3,4,5-hexahydrobenz[cd]indole A. A mixture of 1-benzoyl-4,5-(endo)epoxy-1,2,2a,3,4,5-hexahydrobenz[cd]-indole (21 g, 0.076 mol) and (+)-R-1-phenethylamine (18 g, 0.15 mol) in 400 ml of n-butanol was refluxed under N$_2$ for 16 h. The reaction was concentrated in vacuo to provide 30 g of an oil as an equal mixture of two diastereomeric amino alcohols.

The mixture of amino alcohols was dissolved in 300 ml of CH$_2$Cl$_2$ and Et$_3$N (30 g, 0.225 mol) was added at once under N$_2$. The reaction mixture was cooled to −10° C. then MsCl (12.9 g, 0.011) was slowly added dropwise. The rate of addition was such as to maintain a reaction temperature between −10° and 5° C. Upon complete addition of MsCl, the reaction mixture was stirred for an additional 30 min at −5° C. and then 30 min at ambient temperature. To the reaction mixture was added 200 ml of water and the mixture was stirred. The CH$_2$Cl$_2$ solution was separated and washed successively sat'd NaHCO$_3$ sol and brine sol. The organic sol was dried (MgSO$_4$) and concentrated to dryness to provide a mixture of two diastereomeric aziridines. The mixture was separated by preparative HPLC (silica gel; hexanes/EtOAc gradient). The first diastereomer of the aziridines to be eluted was designated isomer 1; 6.6 g, mp 162°-163° C. from i-PrOH. The second diastereomer to be eluted was designated as isomer 2; 7.4 g, mp 144°-145° C. from isopropyl alcohol.

B. (2aR, 4R)-4-amino-1-benzoyl-1,2,2a,3,4,5-hexahydrobenzl[cd]indole

A solution of aziridine isomer 1 (9.4 g, 0.025 mol) in 90 ml of glacial acetic acid was hydrogenated at 60 psi and at 60° C. over 5% Pd/C for 16h. The reaction mixture was filtered and the filtrate was evaporated to a residual oil. The residue was dissolved in 1N HCl and the acidic mixture was extracted once with EtOAC. The acidic solution was made alkaline with addition of concentrated $NH_4OH$. The basic mixture was extracted with $CH_2Cl_2$. The $CH_2Cl_2$ solution was washed with brine solution and dried ($MgSO_4$). The organic solution was evaporated to dryness to provide 2aR,4R-4-amino-1-benzoyl-1,2,2a,3,4,5-hexhydrobenz[cd]indole; 5.2 g as an oil.

C. (2aR,4R)-4-amino-1-benzoyl-6-bromo-1,2,2a,3,4,5-hexahydrobenz[cd]indole

A solution of (2aR, 4R)-4-amino-1-benzoyl-1,2,2a,3,4,5-hexahydro-benz[cd]indole (5.2 g, 0.019 mol) and sodium acetate (6.2 g, 0.076) in 40 mL glacial acetic acid (HOAc) and 10 mL of MeOH was cooled to 10° C. to the reaction mixture was added dropwise a solution of bromine (3 g, 0.019 mol) in 10 mL of glacial HOAc. The reaction temperature was maintained at 10° C. during addition of the bromine. The reaction was then stirred at ambient temperature for 1 h. The solvents were evaporated and the residue was dissolved in water. The acidic solution was made alkaline with cold 50% aqueous NaOH. The basic mixture was extracted twice with $CH_2Cl_2$. The organic solution was washed with brine solution, dried ($MgSO_4$) and concentrated in vacuo to provide 6.8 g (2aR,4R)-6-bromo compound as an oil.

D. (2aR,4R)-1-benzoyl-6-bromo-4-(di-n-propylamino)-1,2,2a3,4,5-hexahydrobenz[cd]indole A reaction mixture of (2aR,4R)-4-amino-1-benzoyl-6-bromo-1,2,2a,3,4,5-hexahydrobenz[cd]indole(6.8 g, 0.019 mol), $K_2CO_3$(8.28 g, 0.06 mol) and n-propyliodide(10.2 g, 0.06 mol) in 200 mL of $CH_3CN$ was stirred at reflux temperature for 16 h. The reaction mixture was filtered and solvent was evaporated. The residue was dissolved in EtOAc and the solution was extracted with dilute HCl. The acidic solution was made alkaline with concentrated $NH_4OH$. The basic mixture was extracted with EtOAc. The organic solution was washed with brine solution and dried ($MgSO_4$). The EtOAc was evaporated to provide a residual oil. Chromatography (silica gel-EtOAc) gave product, 2.4 g.

E. (2aR,4R)-1-Benzoyl-6-cyano-4-(di-n-propylamino)-1,2,2a,3,4,5-hexahydrobenz[cd]indole To a solution of (2aR,4R)-1-Benzoyl-6-bromo-4-(di-n-propylamino)-1,2,2a,3,4,5-hexa-hydrobenz[cd]indole (2.4 g;5 mmol) in 100 mL of dimethyl formamide (DMF) was added CuCN (1.34 g, 15 mmol) and CuI (2.85 g, 15 mmol). The reaction mixture was stirred at reflux under a $N_2$ atmosphere for 16 hr. The reaction mixture was poured into 500 mL of water. The ppt was collected and washed several times with water. The ppt was suspended in dil $NH_4OH$ and slurried with EtOAc. The whole mixture was filtered thru a celite pad. The EtOAc sol was separated and washed with brine sol. The EtOAc sol was dried($MgSO_4$) and conc to dryness to provide 1.7 g of nitrile as an oil.

F. (2aR,4R)-6-Cyano-4-(di-n-propylamino)-1,2,2a,3,4,5-hexahydrobenz[cd]indole

To a stirred solution of 1.7 g (4.4 mmol) of (2aR,4R)-6-cyano-4-(di-n-propylamino)-1,2,2a,3,4,5-hexahydrobenz[c,d]indole in 25 mL of THF cooled to −78° C. under a $N_2$ atmosphere was added 5.5 mL (8.8 mmol) of 1.6M solution of n-BuLi in hexane. The reaction mixture was stirred at −78° C. for 30 min. and then allowed to warm to −20° C. To the reaction mixture was added 20 mL of 1N HCl. The mixture was extracted once with $Et_2O$. The acidic solution was made alkaline with the addition of cold 5N NaOH. The basic mixture was extracted twice with $CH_2Cl_2$. The combined organic solution was washed with sat'd NaCl solution. The $CH_2Cl_2$ solution was dried over $MgSO_4$ and evaporated to give 1.3 g of an oil. Chromatography of this oil over silica gel with EtOAc as eluent gave 1 g (80%) of product as an oil.

G. (2aR,4R)-1-Trityl-6-cyano-4-(di-n-propylamino)-1,2,2a, 3,4,5-hexahydrobenz[cd]indole To a sol of (2aR,4R)-1-trityl-6-cyano-4-(di-n-propylamino)-1,2,2a,3,4,5-hexahydrobenz[cd]indole (1 g, 3.5 mmol) and $Et_3N$ (354 mg, 3.5 mmol) in 50 mL of methylene chloride was added a sol of triphenylmethyl chloride (trityl chloride) (0.98 g, 3.5 mmol) in 10 mL of methylene chloride dropwise at RT. The reaction mixture was stirred for 16 hr at RT. The reaction mixture was extracted with water and cold 1N HCl. The organic sol was washed with sat'd $NaHCO_3$ sol and with sat'd brine sol. The organic sol was dried ($MgSO_4$) and conc to dryness in vacuo to give a residue. The residue was slurried with warm hexanes, cooled and filtered to remove insolubles. The filtrate was conc to an oil. The oil was chromatographed (silica gel, 20% EtOAc in hexanes) to provide 1.5 g of (2aR,4R)-1-trityl-6-cyano-4-(di-n-propylamino)-1,2,2a,3,4,5-hexahydrobenz-[cd]indole.

H. (2aR,4R)-6-acetyl-4-(di-n-propylamino)-1,2,2a,3,4,5-hexahydrobenz[c,d]indole

A solution of 1.6 g (3 mmol) (2aR,4R)-1-trityl-6-cyano-4-(di-n-propylamino)-1,2,2a,3,4,5-hexahydrobenz[cd]indole in 100 ml of THF was treated with 20 mL of 2.0M methylmagnesium bromide in diethyl ether. The reaction mixture was refluxed for 16 hr. The reaction mixture was cooled and excess Grignard reagent was decomposed with addition of sat'd $NH_4Cl$ solution. The reaction mixture was extracted with EtOAc. The organic solution was evaporated to an oil. The oil was dissolved in 25 mL of 5N HCl and the solution was stirred at room temperature for 30 min. The acidic solution was made alkaline with the addition of excess conc $NH_4OH$ solution. The basic mixture was extracted twice with EtOAc. The combined organic solution was washed once with sat'd NaCl solution and dried over $MgSO_4$. The EtOAc solution was evaporated to yield 0.9 g of an oil. Chromatography of this oil over silica gel with EtOAc as eluent gave 600 mg of product. Recryst from hexanes to yield 228 mg (−) ketone.

mp 85°-86°; $[\alpha]_D = -4.94°$ ($CH_3OH$).

EXAMPLE 5

Preparation of (2aS,4S)-6-acetyl-4-(di-n-propylamino)-1,2,2a,3,4,5-hexahydrobenz[cd]indole A. Aziridine isomer 2 from Example 4A (8.5 g, 0.022 mol) was hydrogenated to provide (2aS,4S)-4-amino-1-benzoyl-1,2,2a,3,4,5-hexahydrobenz[cd]indole (4.5 g) as an oil.

B. (2aS,4S)-4-amino-1-benzoyl-6-bromo-1,2,2a,3,4,5-hexahydrobenz[cd]indole

Using the procedure of Example 4C, (2aS,4S)-4-amino-1-benzoyl-1,2,2a,3,4,5-hexahydrobenz[cd]indole (4.5 g,0.016 mol) was halogenated to yield 5.4 g (2aS,4S)-6-bromo compound as an oil.

C. (2aS,4S)-1-benzoyl-6-bromo-4-(di-n-propylamino)-1,2,2a,3,4,5-hexahydrobenz[cd]indole Using the procedure of Example 4D, the reaction of (2aS,4S)-4-amino-1-benzoyl-6-bromo-1,2,2a,3,4,5-hexahydrobenz[cd]indole(5.4 g, 0.015 mol) with n-propyliodide (10.2 g, 0.06 mol) in the presence of $K_2CO_3$(8.28 g, 0.06 mol) in 200 ml of $CH_3CN$ gave, after chromatography, 3.1 g of product.

D. (2aS,4S)-1-Benzoyl-6-cyano-4-(di-n-propylamino)-1,2,2a,3,4,5-hexahydrobenz[cd]indole Using the procedure of Example 4E, (2aR,4R)-1-benzoyl-6-bromo-4-(di-n-propylamino)-1,2,2a,3,4,5-hexahydrobenz[cd]indole (3.1 g, 7 mmol) with CuCN (1. g,21 mmol) and CuI (4 g, 21 mmol) in 100 ml DMF gave 2.5 g of nitrile as an oil.

E. (2aS,4S)-6-Cyano-4-(di-n-propylamino)-1,2,2a,3,4,5-hexahydrobenz[cd]indole

The procedure of Example 4F was followed using 2.5 g (6.5 mmol) of (2aS,4S)-1-benzoyl-6-cyano-4-(di-n-propylamino)-1,2,2a,3,4,5-hexahydrobenz[cd]-indole and 8.1 ml (13 mmol) n-butyl lithium to provide 1.6 g of an oil. Chromatography of the oil over silica gel with EtOAc as eluent gave 1 g (54%) of product as an oil.

F. (2aS,4S)-1-trityl-6-cyano-4-(di-n-propylamino)-1,2,2a,3,4,5-hexahydrobenz [cd]indole The procedure of Example 4 G was followed using the product from Example 4E (1 g, 3.5 mmol) to provide 1.6 g of product.

G. Formation of (2aS,4S)-6-acetyl-4-(di-n-propylamino)-1,2,2a,3,4,5-hexahydrobenz[cd]indole The procedure of Example 4H was followed using product from Example 4F (1.6 g, 2.9 mmol) to provide 1.0 g of an oil. Chromatography of the oil over silica gel with EtOAc as eluent gave 700 mg of product. Recrystallization from hexanes yielded 240 mg of the (+) ketone.

mp 85°–86° C.
$[\alpha]_D$= +5.15°($CH_3OH$).

EXAMPLE 6

Preparation of (+)-(2aS,4R)-6-acetyl-4-(di-n-propylamino)-1,2,2a,3,4,5-hexahydrobenz[cd]indole.

The above described procedure was used to prepare (2aS,4R)-1-benzoyl-6-bromo-4-(di-n-propylamino)-1,2,2a,3,4,5-hexahydrobenz[cd]indole. The procedures of Example 4 were used to form (+) (2aS,4R)-1-trityl-6-cyano-4-(di-n-propylamine)-1,2,2a,3,4,5-hexahydrobenz[cd]indole a solution of which (2.4 g,4.6 mmol) in 100 ml of THF was treated with 25 mL of 2.0M methylmagnesium bromide in diethyl ether. The reaction mixture was refluxed for 16 hr. The reaction mixture was cooled and excess Grignard reagent was decomposed with addition of saturated $NH_4Cl$ solution. The reaction mixture was extracted with ethyl acetate. The organic solution was evaporated to an oil. The oil was dissolved in 25 mL of 5N HCl and the solution was stirred at room temperature for 30 min. The acidic solution was made alkaline with the addition of excess concentrated $NH_4OH$ solution. The basic mixture was extracted twice with ethyl acetate. The combined organic solution was washed once with saturated NaCl solution and dried over $MgSO_4$. The ethyl acetate solution was evaporated to yield 1.4 g of an oil. Chromatography of this oil over silica gel with ethyl acetate as eluent gave 1.2 g (87%) of product. Recrystallization from hexane yielded 840 mg of the product (+) ketone.

mp=121°–122° C.
$[\alpha]_D$= +66.60° ($CH_3OH$).

EXAMPLE 7

Preparation of (−) (2aR,4S)-6-acetyl-4-(di-n-propylamino)-1,2,2a,3,4,5-hexahydrobenz[cd]indole The above described procedure was used to prepare (2aR,4S)-1-benzoyl-6-bromo-4-(di-n-propylamino)-1,2,2a,3,4,5-hexahydrobenz[cd]indole. The procedures of Example 4 were used to prepare (2aR,4S)-1-trityl-6-cyano-4-(di-n-propylamino)-1,2,2a,3,4,5-hexahydrobenz[cd]indole a solution of which (3.4 g,6.5 mmol) in 100 ml of THF was treated with 40 mL of 2.0M methylmagnesium bromide in diethyl ether. The reaction mixture was refluxed for 16 hr. The reaction mixture was cooled and excess Grignard reagent was decomposed with addition of sat'd $NH_4Cl$ solution. The basic mixture was extracted twice with EtOAc. The combined organic solution was washed once with sat'd NaCl solution and dried over $MgSO_4$. The EtOAc solution was evaporated to yield 1.9 g of an oil. Chromatography of this oil over silica gel with EtOAc as eluent gave 1.8 g of product which was recrystallized from hexane to yield 1.4 g of product.

mp 120°–121° C.
$[\alpha]_D$= −64.48°($CH_3OH$).

EXAMPLE 8

Preparation of (+)-(2aS,4R)-6-(2-methylpropanoyl)-4-(di-n-propylamino)-1,2,2a,3,4,5-hexahydrobenz[cd]indole (2aS,4R)-1-trityl-6-cyano-4-(di-n-propylamino)-1,2,2a,3,4,5-hexahydrobenz[cd]indole was prepared as in Example 6. A solution of this hexahydrobenz[cd]indole (9.5 g,0.018 mol) in 200 mL of THF was treated with 30 mL of 2.0M isopropylmagnesium chloride in diethyl ether. The reaction mixture was refluxed for 16 hr. The reaction mixture was cooled and decomposed with addition of 50 mL of 5N HCl then warmed for 30 min on a steam bath. The acidic mixture was extracted twice with EtOAc. The combined organic solution was washed once with sat'd NaCl solution and dried over $MgSO_4$. The EtOAc solution was evaporated to yield 1.9 g of an oil. Chromatography of this oil over silica gel with EtOAc as eluent gave 0.9 g of product. Recrystallization from hexanes to yield 360 mg of product.

mp 87°–89° C.
$[\alpha]_D$= +52.72° ($CH_3OH$).

EXAMPLE 9

Preparation of
(−)-6-(2-methylpropanoyl)-4-(di-n-propylamino)-
1,2,2a,3,4,5-hexahydrobenz[cd]indole The procedure of Example 8 was followed with (−)-1-trityl-6-cyano-4-(di-n-propylamino)-1,2,2a,3,4,5-hexahydrobenz[cd]indole (7 g,13 mmol), isopropylmagnesium chloride (50 mL, 2 molar in ethyl ether), THF (150 mL) to give 3.8 g of crude product. Chromatography with silica gel using EtOAc as eluent gave 0.8 g of material which was recrystallized from hexanes to give 400 mg of product.

mp=88°-89° C.
$[\alpha]_D = -51.0°$ (CH$_3$OH).

EXAMPLE 10

Preparation of
(−)-(2aR,4S)-6-(propanoyl)-4-(di-n-propylamino)-
1,2,2a,3,4,5-hexahydrobenz[cd]indole A solution of (−)-(2aR, 4S)-1-trityl-6-cyano-4-(di-n-propylamino)-1,2,2a,3,4,5-hexahydrobenz[c,d]indole (1.5 g, 2.7 mmol) in 200 ml of THF was treated with 25 mL of 2.0M ethylmagnesium bromide in diethyl ether. The reaction mixture was refluxed for 16 hr. The reaction mixture was cooled and decomposed with addition of 50 mL of 5N HCl then warmed for 30 min on a steam bath. The acidic mixture was extracted with EtOAc. The acidic solution was made alkaline with the addition of excess conc NH$_4$OH solution. The basic mixture was extracted twice with EtOAc. The combined organic solution was washed once with sat'd NaCl solution and dried over MgSO$_4$. The EtOAc solution was evaporated to yield 0.6 g of an oil. Chromatography of this oil over silica gel with EtOAc as eluent gave 0.4 g of product. Recrystallization from hexanes gave 300 mg (−) ketone.

mp 90°-91° C.
$[\alpha]_D = -63.68°$ (CH$_3$OH).

EXAMPLE 11

Preparation of
(+)-(2aS,4R)-6-(pentanoyl)-4-(di-n-propylamino)-
1,2,2a,3,4,5-hexahydrobenz[cd]indole A solution of (+)-(2aS,4R)-1-triethyl-6-cyano-4-(di-n-propylamino)-1,2,2a,3,4,5-hexahydrobenz[cd]indole (1.0 g, 2 mmol) in 40 ml of THF was added dropwise to a solution of n-butylmagnesium iodide (25 mmol) in 25 mL diethyl ether. The reaction mixture was refluxed for 16 hr. The reaction mixture was cooled and decomposed with addition of 50 mL of 5N HCl then warmed for 30 min on a steam bath. The acidic mixture was extracted with EtOAc. The acidic solution was made alkaline with the addition of excess conc NH$_4$OH solution. The basic mixture was extracted twice with EtOAc. The combined organic solution was washed once with sat'd NaCl solution and dried over MgSO$_4$. The EtOAc solution was evaporated to yield 0.4 g of an oil. Chromatography of this oil over silica gel with EtOAc as eluent gave 70 mg of product. Recrystallization from hexane gave 25 mg ketone. mp 104°-105° C.
$[\alpha]_D = +35.7°$(CH$_3$OH).

EXAMPLE 12

Preparation of
(+)-(2aS,4R)-6-(benzoyl)-4-(di-n-propylamine)-
1,2,2a,3,4,5-hexahydrobenz[cd]indole A solution of (+)-(2aS,4R)-1-trityl-6-cyano-4-(di-n-propylamino)-1,2,2a,3,4,5-hexahydrobenz[cd]indole (1.5 g, 2.7 mmol) in 30 mL of THF was treated with 10 mL of 3.0M phenylmagnesium bromide in diethyl ether. The reaction mixture was refluxed for 16 hr. The reaction mixture was cooled and decomposed with addition of 50 mL of 5N HCl then warmed for 30 min on a steam bath. The acidic mixture was extracted with EtOAc. The acidic solution was made alkaline with the addition of excess conc NH$_4$OH solution. The basic mixture was extracted twice with EtOAc. The combined organic solution was washed once with sat'd NaCl solution and dried over MgSO$_4$. The EtOAc solution was evaporated to yield 0.6 g of an oil. Chromatography of this oil over silica gel with EtOAc as eluent gave 0.3 g of product. Recrystallization from hexanes gave 360 mg (+) ketone.

mp 161°-162° C.
$[\alpha]_D = +93.66°$ (CH$_3$OH).

EXAMPLE 13

Preparation of
(+)-(2aS,4R)-6-(2-phenylethanoyl)-4-(di-n-propylamino)-1,2,2a,3,4,5-hexahydrobenz[cd]indole A solution of (+)-(2aS,4R)-1-trityl-6-cyano-4-(di-n-propylamino)-1,2,2a,3,4,5-hexahydrobenz[c,d]indole (1.0 g,2 mmol) in 40 mL of THF was added dropwise to a solution of benzylmagnesium chloride (25 mmol) in 25 mL diethyl ether. The reaction mixture was refluxed for 16 hr. The reaction mixture was cooled and decomposed with addition of 50 mL of 5N HCl then warmed for 30 min on a steam bath. The acidic mixture was extracted with EtOAc. The acidic solution was made alkaline with the addition of excess conc NH$_4$OH solution. The basic mixture was extracted twice with EtOAc. The combined organic solution was washed once with sat'd NaCl solution and dried over MgSO$_4$. The EtOAc solution was evaporated to yield 0.6 g of an oil. Chromatography of this oil over silica gel with EtOAc as eluent gave 0.4 g of product. Recrystallization from hexanes gave 225 mg (+) ketone.

mp 104°-105° C.
$[\alpha]_D = +47.62°$ (CH$_3$OH).

EXAMPLE 14

Preparation of
(2aS,4R)-6-ethynyl-4-(di-n-propylamino)-1,2,2a,3,4,5-hexahydrobenz[cd]indole 1-benzoyl-(2aS,4R)-6-iodo-4-(di-n-propylamino)-1,2,2a,3,4,5-hexahydrobenz[cd]indole (100 mg, 0.205 mmol) and trimethyltin acetylene trimethylsilane (272 mg, 1.0 mmol, 3 eq) was dissolved in anhydrous toluene (5 mL), to which was then added tetrakis-triphenylphosphine palladium (20 mg, 0.017 mmol, 0.05 eq). The resulting light yellow solution was brought to reflux under N$_2$ atmosphere. After 4 hr, the reaction mixture was cooled to room temperature, filtered and concentrated to dryness. The residue was chromatographed over silica gel with hexanes:ethyl acetate (1:1) to afford the desired product (79 mg, 84%). This material was dissolved in a 1N solution (5 mL) of tetrabutylammonium fluoride in THF, and stirred at room temperature overnight (12 h). The solution was diluted with EtOAc (10 mL) and rinsed successively with H$_2$O (3×10 mL), brine (10 mL) and dried over Na$_2$SO$_4$. The residue was chromatographed over silica gel with hexanes:ethyl acetate (1:1) to afford a mixture of the 1-benzoyl (61%) and the N-deprotected indoline (33%).

The present compounds of Formula I have been found to have selective affinity for the 5HT receptors in the brain with much less affinity for other receptors. Because of their ability to selectively bind to 5HT receptors, the compounds of Formula I are useful in treating disease states which require alteration of 5-HT$_{1A}$ receptor function but without the side effects which may be associated with less selective compounds. It has been further found that certain of the instant compounds have substantial affinity for both the 5-HT$_{1A}$ and 5-HT$_{1D}$ receptors and are useful in treating disease states which can benefit from an alteration of the receptors. The alteration of the 5HT$_{1A}$ and 5HT$_{1D}$ receptors may involve mimicking (an agonist) or inhibiting (an antagonist) the function of serotonin. The disease states include anxiety, depression, excess gastric acid secretion, hypertension, nausea, sexual dysfunction, cognition, senile dementia, consumptive disorders such as appetite disorders, alcoholism and smoking. The foregoing conditions are treated with a pharmaceutically effective amount of a compound of Formula I.

The term "pharmaceutically effective amount", as used herein, represents an amount of a compound of the invention which is capable of diminishing the adverse symptoms of the particular disease. The particular dose of compound administered according to this invention of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for prophylactic treatment, however, will contain from about 0.01 mg/kg to about 50 mg/kg of the active compound of this invention when administered orally. Preferred oral doses will be about 0.01 to about 3.0 mg/kg, ideally about 0.01 to about 0.1 mg/kg. When a present compound is given orally it may be necessary to administer the compound more than once each day, for example about every eight hours. For IV administration by bolus, the dose will be from about 10 μg/kg to about 300 μg/kg, preferably about 20 μg/kg to about 50 μg/kg.

The following experiments were conducted to demonstrate the ability of the compounds of the present invention to interact with the serotonin 1A and/or 1D receptors. The affinities of the compounds at the central 5-HT$_{1A}$ receptors were determined using a modification of the binding assay described by Taylor, et al., (J. Pharmacol. Exp. Ther. 236:118-125, 1986). Membranes for the binding assay were prepared from male Sprague-Dawley rats (150-250 g). The animals were killed by decapitation, and the brains were rapidly chilled and dissected to obtain the hippocampi. The hippocampi were either prepared that day or stored frozen (−70° C.) until the day of preparation. Membranes were prepared by homogenizing the tissue in 40 volumes of ice-cold Tris-HCl buffer (50 mM, pH 7.4 at 22° C.) using a Techmar Tissumizer (setting 65 for 15 sec), and the homogenate was centrifuged at 39800×g for 10 min. The resulting pellet was then resuspended in the same buffer, and the centrifugation and resuspension process was repeated three additional times to wash the membranes. Between the second and third washes the resuspended membranes were incubated for 10 min at 37° C. to facilitate the removal of endogenous ligands. The final pellet was resuspended in 67 mM Tris-HCl, pH 7.4, to a concentration of 2 mg of tissue original wet weight/200 μl. This homogenate was stored frozen (−70° C.) until the day of the binding assay. Each tube for the binding assay had a final volume of 800 μl and contained the following: Tris-HCl (50 mM), pargyline (10 μM), CaCl$_2$ (3 mM), [$^3$H]8-OH-DPAT (1.0 nM), appropriate dilutions of the compound being evaluated, and membrane resuspension equivalent to 2 mg of original tissue wet weight, for a final pH of 7.4. The assay tubes were incubated for 10 min at 37° C., and the contents were then rapidly filtered through GF/B filters (pretreated with 0.5% polyethylenimine), followed by four one-mL washes with ice cold buffer. The radioactivity trapped by the filters was quantitated by liquid scintillation spectrometry, and specific [$^3$H]8-OH-DPAT binding to the 5-HT$_{1A}$ sites was defined as the difference between [$^3$H]8-OH-DPAT bound in the presence and absence of 10 μM 5-HT.

The affinity of the particular compound at the 5-HT$_{1A}$ receptor is expressed as IC$_{50}$ value, i.e., the concentration required to inhibit 50% of the binding. The IC$_{50}$ values were determined from 12-point competition curves using nonlinear regression (SYSTAT, SYSTAT, INC., Evanston, Ill.). The results from this determination are provided in Table I.

The affinities of the compounds at the central 5-HT$_{1D}$ binding sites were determined using a modification of the binding assay described by Heuring and Peroutka (J. Neurosci. 7:894-903, 1987). Bovine brains were obtained from Pel-Freeze Biologicals, and the caudate nuclei were dissected out and frozen at −70° C. until the time that the membranes were prepared for the binding assays. At that time the tissues were homogenized in 40 volumes of ice-cold Tris-HCl buffer (50 mM, pH 7.4 at 22° C.) with a Techmar Tissumizer (setting 65 for 15 sec), and the homogenate was centrifuged at 39,800 g for 10 min. The resulting pellet was then resuspended in the same buffer, and the centrifugation and resuspension process was repeated three additional times to wash the membranes. Between the second and third washes the resuspended membranes were incubated for 10 min at 37° C. to facilitate the removal of endogenous 5-HT. The final pellet was resuspended in Tris buffer to a concentration of 25 mg of original tissue wet weight/ml for use in the binding assay. Each tube for the binding assay had a final volume of 800 μl and contained the following: Tris-HCl (50 mM), pargyline (10 μM), ascorbate (5.7 mM), CaCl$_2$ (3 mM), 8-OH-DPTA (100 nM to mask 5-HT$_{1A}$ receptors), mesulergine (100 nM to mask 5-HT$_{1C}$ receptors), [$^3$H]5-HT (1.7-1.9 nM), appropriate dilutions of the drugs of interest, and membrane suspension equivalent to 5 mg of original tissue wet weight, for a final pH of 7.4. The assay tubes were incubated for 10 min at 37° C., and the contents were then rapidly filtered through GF/B filters (pretreated with 0.5% polyethylenimine), followed by four one-mL washes with ice-cold buffer. The radioactivity trapped by the filters was quantitated by liquid scintillation spectrometry, and specific [$^3$H]5-HT binding to the 5-HT$_{1D}$ sites was defined as the difference between [$^3$H]5-HT bound in the presence and absence of 10 μM 5-HT.

The affinities of compounds at the 5-HT1D receptor are expressed as IC$_{50}$ values, i.e., the concentration required to inhibit 50% of the binding. These values were determined from 12-point competition curves using nonlinear regression (SYSTAT, SYSTAT, Inc., Evanston, Ill.). The results from this determination are provided in Table I.

TABLE I

| Example No. | 5HT$_{1A}$[1] | 5HT$_{1D}$[1] |
| --- | --- | --- |
| 3 | 0.63 | 7.47 |
| 4 | 0.80 | 236.38 |
| 5 | 0.31 | 129.24 |
| 6 | 0.3 | 6.25 |
| 7 | 6.61 | 8500.0 |
| 8 | 0.25 | 1.24 |
| 9 | 54.88 | 3125.00 |
| 10 | 9.47 | 9000.00 |
| 12 | 0.34 | 1.78 |
| 13 | 0.98 | 2.7 |

[1]IC$_{50}$ in nanomoles per liter

The compound of Example 14 was evaluated for its ability to interact with serotonin 1A receptor using the following procedure which is generally set forth in Wong et al., *J. Neural Transm.*, 71, 207–218 (1988). Male Sprague-Dawley rats (110–150 g) from Harlan Industries (Cumberland, Ill.) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000×g for 10 min and then at 17,000×g for 20 min, a crude synaptosomal fraction was sedimented. The pellet was suspended in 100 vol of 50 mM Tris-HCl, pH 7.4, incubated at 37° C. for 10 min, and centrifuged at 50,000×g for 10 min. The process was repeated and the final pellet was suspended in ice-chilled 50 mM Tris-HCl, pH 7.4. By the radioligand binding method, sites specifically labeled by tritiated 8-hydroxy-2-dipropylamino-1,2,3,4-tetrahydronaphthalene ($^3$H-8-OH-DPAT) have been identified as 5-HT$_{1A}$ receptors.

Binding of ($^3$H-8-OH-DPAT) was performed according to the previously described method [Wong et al., *J. Neural Transm.* 64:251–269 (1985)]. Briefly, synaptosomal membranes isolated from cerebral cortex were incubated at 37° C. for 10 min. in 2 mL of 50 mM Tris-HCl, pH 7.4; 10 μM pargyline; 0.6 mM ascorbic acid; 0.4 nM $^3$H-8-OH-DPAT; and from 1 to 1000 mM of test compound. Binding was terminated by filtering samples under reduced pressure through glass fiber (GFB) filters. The filters were washed twice with 5 mL of ice cold buffer and placed in scintillation vials with 10 mL of PCS (Amersham/Searle) scintillation fluid. Radioactivity was measured with a liquid scintillation spectrometer. Unlabeled 8-OH-DPAT at 10 μM was also included in separate samples to establish non-specific binding. Specific binding of $^3$H-8-OH-DPAT is defined as the difference of radioactivity bound in the absence and in the presence of 10 μM unlabeled 8-OH-DPAT.

The result is provided in Table II. The value is the IC$_{50}$, i.e. the concentration in nanomoles of the compound necessary to inhibit the binding of $^3$H-8-OH-DPAT by 50%.

TABLE II

| Example | IC$_{50}$ |
| --- | --- |
| 14 | 0.5 |

Experiments were conducted to demonstrate the serotonin against properties of the instant compounds. Certain compounds were evaluated to determine their ability to affect the 5-hydroxyindoles serotonin, 5-hydroxyindole acetic acid (5HIAA) and serum corticosterone, in vivo, using the following procedures.

Compounds in aqueous solution were injected subcutaneously into male albino rats. Rats were decapitated one hour later. Trunk blood was collected and allowed to clot; after centrifugation, serum was stored frozen prior to analysis. Whole brain was removed and frozen on dry ice, then stored frozen prior to analysis. Serum corticosterone concentration was measured spectrofluorometrically (J. H. Solem and T. Brinch-Johnsen, "An evaluation of a method for determination of free corticosteroids in minute quantities of mouse plasma," *Scand. J. Clin. Lab. Invest.* (Suppl. 80), 1.14 (1965).) 5-Hydroxyindoleacetic acid (5HIAA) concentration in whole brain was measured by liquid chromatography with electrochemical detection. (Ray W. Fuller and Kenneth W. Perry, "Effects of buspirone and its metabolite, 1-(2-pyrimidinyl)piperazine, on brain monoamines and their metabolites in rats", *J. Pharmacol. Exp. Ther.* 248, 50–56 (1989).) The results are provided in Table III.

TABLE III

| Example No. (dose mg/Kg) | Brain 5-hydroxyindoles (n moles/g) | | Serum Corticosterone (μg/100 ml) |
| --- | --- | --- | --- |
| | Serotonin | 5-HIAA | |
| Control | 2.76 ± 0.12 | 2.13 ± 0.10 | 3.8 ± 0.2 |
| Example 6 | | | |
| (0.003) | 2.46 ± 0.14 | 1.81 ± 0.14 | 5.8 ± 1.0 |
| (0.03) | 2.99 ± 0.06 | 1.58 ± 0.08* | 10.6 ± 2.0* |
| (0.3) | 3.08 ± 0.04* | 1.41 ± 0.03* | 42.2 ± 1.1* |
| Example 7 | | | |
| (0.003) | 2.75 ± 0.05 | 2.06 ± 0.13 | 3.8 ± 0.5 |
| (0.03) | 2.57 ± 0.10 | 1.87 ± 0.07 | 6.5 ± 2.6 |
| (0.3) | 2.85 ± 0.08 | 1.77 ± 0.17 | 8.4 ± 4.0 |
| Control | 1.66 ± 0.04 | 1.68 ± 0.12 | 3.4 ± 0.2 |
| Example 8 | | | |
| (0.003) | 1.88 ± 0.05* | 1.56 ± 0.10 | 3.6 ± 0.7 |
| (0.03) | 2.26 ± 0.06* | 1.34 ± 0.06* | 27.1 ± 6.4* |
| (0.3) | 2.26 ± 0.16* | 1.30 ± 0.07* | 42.0 ± 0.4* |
| Example 9 | | | |
| (0.003) | 1.83 ± 0.08 | 1.68 ± 0.10 | 4.1 ± 0.5 |
| (0.03) | 1.90 ± 0.10 | 1.91 ± 0.06 | 6.0 ± 1.6 |
| (0.3) | 1.69 ± 0.06 | 1.74 ± 0.04 | 6.7 ± 2.0 |

*Significant difference from control group (P<0.05)

The compounds of the present invention are preferably formulated prior to administration. Therefore, yet another embodiment of the present invention is a pharmaceutical formulation comprising a compound of the invention and a pharmaceutically acceptable excipient therefor.

The present pharmaceutical formulations are prepared by known procedures using well known and readily available ingredients. In making the compositions of the present invention, the active ingredient will usually be mixed with an excipient, diluted by an excipient or enclosed within such a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelating capsules, suppositories, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 50 mg, more usually about 1 to about 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| 6-acetyl-4-(di-n-propylamino)-1,2,2a,3,4,5-hexahydrobenz[cd]indole | 25 |
| Starch, dried | 425 |
| Magnesium stearate | 10 |
| Total | 460 mg | into hard gelatin capsules in 460 mg quantities.

FORMULATION 2

A tablet formula is prepared using the ingradients below:

| | Quantity (mg/tablet) |
|---|---|
| 4-(di-n-propylamino)-6-(2,2-dimethylpropanoyl)-1,2,2a,3,4,5-hexahydrobenz[cd]indole | 25 |
| Cellulose, microcrystalline | 625 |
| Colloidal Silicon Dioxide | 10 |
| Stearic acid | 5 |

The components are blended and compressed to form tablets each weighing 665 mg.

FORMULATION 3

A dry powder inhaler formulation is prepared containing the following components:

| | Weight % |
|---|---|
| 4-(diethylamino)-6-propanoyl-1,2,2a,3,4,5-hexahydrobenz[cd]indole | 5 |
| Lactose | 95 |

The active compound is mixed with the lactose and the mixture added to a dry powder inhaling applicance.

FORMULATION 4

Tablets each containing 60 mg of active ingredient are made up as follows:

| | |
|---|---|
| 4-(n-propylamino)-6-(2-methyl-propanoyl)-1,2,2a,3,4,5-hexahydrobenz[cd]indole tartrate salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°-60° C. and passed through a No. 16 mesh U.S. sieve. The sodium carboxymethyl starch, magnesium stearate and talc, previously passed through a No. 30 mesh U.S. sieve, are then added to the granuleswhich, after mixing, are compressed on a tablet machine to yield tablets each weighing 150 mg.

FORMULATION 5

Capsules each containing 20 mg of medicament are made as follows:

| | |
|---|---|
| (2aS,4R)-4-(di-n-propylamino)-6-(2,2-dimethylpropanoyl)-1,2,2a,3,4,5-hexahydrobenz-(cd)indole | 20 mg |
| Starch | 169 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

FORMULATION 6

Suppositories each containing 225 mg of active ingredient are made as follows:

| | |
|---|---|
| 4-(di-n-propylamino)-6-benzoyl-1,2,2a,3,4,5-hexahydrobenz[cd]indole | 225 mg |
| Saturated fatty acid | 2,000 mg |

-continued

| | |
|---|---|
| glycerides to | |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 mL dose are made as follows:

| | |
|---|---|
| 1-methyl-4-(n-propylamino)-6-(3-methylbutanoyl)-1,2,2a,3,4,5-hexahydrobenz[cd]indole | 50 mg |
| Xanthan Gum | 4 mg |
| Sodium carboxymethyl cellulose (11%) | |
| Microcrystalline Cellulose (89%) | 50 mg |
| Sucrose | 1.75 g |
| Sodium Benzoate | 10 mg |
| Flavor | q.v. |
| Color | q.v. |
| Purified water to | 5 mL |

The medicament, sucrose and xanthan gum are blended, passed through a No. 10 mesh U.S. sieve, and then mixed with a previously made solution of the microcrystalline cellulose and sodium carboxymethyl-cellulose in water. The sodium benzoate, flavor and color are diluted with some of the water and added with stirring. Sufficient water is then added to produce the required volume.

FORMULATION 8

Capsules each containing 150 mg of medicament are made as follows:

| | |
|---|---|
| 4-(di-n-propylamino)-6-acetyl-1,2,2a,3,4,5-hexahydrobenz[cd]-indole | 50 mg |
| Starch | 507 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules in 560 mg quantities.

We claim:

1. A compound of the formula I

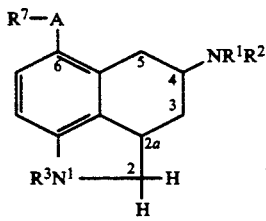

wherein:

$R^1$ is hydrogen, $C_1$-$C_4$ alkyl, $C_3$-$C_4$ alkenyl, cyclopropylmethyl, phenyl-substituted ($C_1$-$C_4$ alkyl), —C(O)$R^4$, —(CH$_2$)$_n$S($C_1$-$C_4$ alkyl), or —(CH$_2$)$_n$-C(O)NR$^5$R$^6$;

$R^2$ is hydrogen, $C_1$-$C_4$ alkyl, $C_3$-$C_4$ alkenyl, or cyclopropylmethyl;

$R^3$ is hydrogen or $C_1$-$C_4$ alkyl;

n is 1-4;

$R^4$ is hydrogen, $C_1$-$C_4$ alkyl, $C_1$-$C_4$ haloalkyl, $C_1$-$C_4$ alkoxy or phenyl;

$R^5$ and $R^6$ are independently hydrogen, a $C_1$-$C_4$ alkyl, or a $C_5$-$C_8$ cycloalkyl;

A is C=O, CHOH or C≡C;

$R^7$ is $C_1$-$C_8$ alkyl, trifluoromethyl, $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, $C_3$-$C_7$ cycloalkyl-substituted methyl, or $C_3$-$C_7$ cycloalkyl, with the proviso that when A is C≡C then $R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl ($C_1$-$C_3$ alkyl), aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, or $C_3$-$C_7$ cycloalkyl; or a pharmaceutically acceptable salt thereof.

2. The compound of claim 1 wherein A is C=O or a pharmaceutically acceptable salt thereof.

3. The compound of claim 2 wherein $R^1$ and $R^2$ are independently hydrogen, $C_1$-$C_4$ alkyl, $C_3$-$C_4$ alkenyl, —(CH$_2$)$_n$S($C_1$-$C_4$ alkyl) or cyclopropylmethyl;

$R^3$ is hydrogen or $C_1$-$C_3$ alkyl; n is 2-4; or a pharmaceutically acceptable salt thereof.

4. The compound of claim 3 wherein:

$R^7$ is $C_1$-$C_4$ alkyl, trifluoromethyl $C_1$-$C_3$ alkoxy-substituted ($C_1$-$C_4$ alkyl), phenyl, phenyl ($C_1$-$C_4$ alkyl), halo-substituted phenyl ($C_1$-$C_4$ alkyl) or $C_3$-$C_7$ cycloalkyl or a pharmaceutically acceptable salt thereof.

5. A substantially pure stereoisomer of the compound of claim 1 or a pharmaceutically acceptable salt thereof.

6. The stereoisomer of claim 5 wherein the configuration at position 2a is S and at position 4 is R.

7. The compound of claim 1 wherein A is C=O; $R^1$ and $R^2$ are independently $C_2$-$C_3$ alkyl; $R^3$ is hydrogen; $R^7$ is $C_1$-$C_3$ alkyl; or a pharmaceutically acceptable salt thereof.

8. The compound of claim 7 wherein $R^1$ and $R^2$ are each n-propyl; $R^7$ is methyl or ethyl; or a pharmaceutically acceptable salt thereof.

9. A compound of claim 1 selected from the group consisting of 4-(di-n-propylamino)-6-acetyl-1,2,2a,3,4,5-hexahydrobenz[cd]indole; 4-(di-n-propylamino)-6-(2,2-dimethylpropanoyl)-1,2,2a,3,4,5-hexahydrobenz[cd]indole; 4-(diethylamino)-6-propanoyl-1,2,2a,3,4,5-hexahydrobenz[cd]indole; 4-(di-n-propylamino)-6-benzoyl-1,2,2a,3,4,5-hexahydrobenz[cd]indole; 4-(n-propylamino)-6-(2-methylpropanoyl)-1,2,2a,3,4,5-hexahydrobenz[cd]indole; 4-(n-propylamino)-6-(3-methylbutanoyl)-1,2,2a,3,4,5-hexahydrobenz[cd]indole; (2aS,4R)-4-(di-n-propylamino)-6-(2,2-dimethyl-propanoyl)-1,2,2a,3,4,5-hexahydrobenz[cd]indole; (2aS,4R)-4-(di-n-propylamino)-6-benzoyl-1,2,2a,3,4,5-hexahydrobenz[cd]indole; 4-(N-n-propyl-N-cyclopropylmethyl)amino-6-propanoyl-1,2,2a,3,4,5-hexahydrobenz[cd]indole; or a pharmaceutically acceptable salt thereof.

10. A compound of claim 1 of the formula

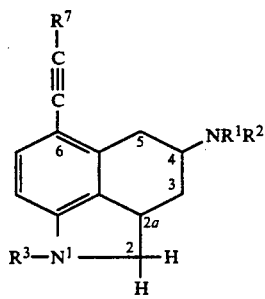

wherein
$R^1$ and $R^2$ are independently hydrogen, $C_1$-$C_4$ alkyl, $C_3$-$C_4$ alkenyl, or cyclopropylmethyl;
$R^3$ is hydrogen or $C_1$-$C_4$ alkyl;
$R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl ($C_1$-$C_3$ alkyl), aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl) substituted with one or two moieties indepentently selected from $C_1$-$C_3$ alkoxy, halo, hydroxy, $C_1$-$C_3$ alkylthio, $C_1$-$C_3$ alkyl and trifluoromethyl or $C_3$-$C_7$ cycloalkyl; or a pharmaceutically acceptable salt thereof.

11. A compound of claim 10 wherein:
$R^1$ and $R^2$ are independently $C_1$-$C_3$ alkyl;
$R^3$ is hydrogen; and
$R^7$ is $C_1$-$C_7$ alkyl, $C_1$-$C_3$ alkoxy-substituted ($C_1$-$C_7$ alkyl), phenyl, phenyl ($C_1$-$C_3$ alkyl), halo-substituted phenyl ($C_1$-$C_3$ alkyl) or $C_3$-$C_7$ cycloalkyl.

12. A substantially pure stereoisomer of the compound of claim 10 wherein the configuration at position 2a is S and at position 4 is R.

13. A compound of claim 1 of the formula

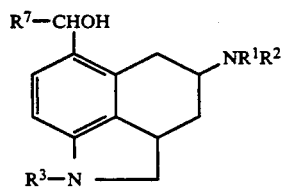

wherein:
$R^1$ and $R^2$ are independently hydrogen, $C_1$-$C_4$ alkyl, $C_3$-$C_4$ alkenyl, or cyclopropylmethyl;
$R^3$ is hydrogen or $C_1$-$C_4$ alkyl;
$R^7$ is $C_1$-$C_8$ alkyl, trifluoromethyl $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl or $C_3$-$C_7$ cycloalkyl; or a pharmaceutically acceptable salt thereof.

14. A compound of claim 13 wherein:
$R^1$ and $R^2$ are independently $C_1$-$C_4$ alkyl; and
$R^3$ is hydrogen.

15. A compound of the Formula I

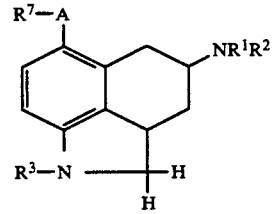

wherein
$R^1$ is hydrogen, $C_1$-$C_4$ alkyl, $C_3$-$C_4$ alkenyl, cyclopropylmethyl, phenyl-substituted ($C_1$-$C_4$ alkyl), —C(O)$R^4$, —(CH$_2$)$_n$S($C_1$-$C_4$ alkyl), or —(CH$_2$)$_n$-C(O)NR$^5$R$^6$;
$R^2$ is hydrogen, $C_1$-$C_4$ alkyl, $C_3$-$C_4$ alkenyl, or cyclopropylmethyl;
$R^3$ is an amino-blocking group;
n is 1-4;
$R^4$ is hydrogen, $C_1$-$C_4$ alkyl, $C_1$-$C_4$ haloalkyl, $C_1$-$C_4$ alkoxy or phenyl;
$R^5$ and $R^6$ are independently hydrogen, $C_1$-$C_4$ alkyl, or $C_5$-$C_8$ cycloalkyl;
A is C=O, CHOH or C≡C;
$R^7$ is $C_1$-$C_8$ alkyl, trifluoromethyl $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, $C_3$-$C_7$ cycloalkyl-substituted methyl, or $C_3$-$C_7$ cycloalkyl with the proviso that when A is C≡C then $R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl), aryl ($C_1$-$C_3$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, or $C_3$-$C_7$ cycloalkyl; or
a pharmaceutically acceptable salt thereof.

16. A compound of claim 15 wherein A is C=O or a pharmaceutically acceptable salt thereof.

17. A compound of claim 15 wherein A is CHOH or a pharmaceutically acceptable salt thereof.

18. A compound of claim 15 wherein A is C≡C or a pharmaceutically acceptable salt thereof.

19. A method for treating a human suffering from anxiety said method comprising administering to said human an effective antianxiety dose of a compound of claim 1.

20. A method for treating a human suffering from depression said method comprising administering to said human an effective antidepressive dose of a compound of claim 1.

21. A pharmaceutical formulation comprising a compound of claim 1 in combination with a pharmaceutically acceptable excipient.

22. The formulation of claim 21 which comprises a compound of the formula

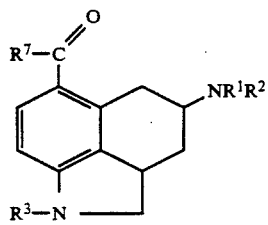

wherein

R$^1$ is hydrogen, C$_1$-C$_4$ alkyl, C$_3$-C$_4$ alkenyl, cyclopropylmethyl, phenyl-substituted (C$_1$-C$_4$ alkyl), —C(O)R$^4$, —(CH$_2$)$_n$S(C$_1$-C$_4$ alkyl), or —(CH$_2$)$_n$-C(O)NR$^5$R$^6$;

R$^2$ is hydrogen, C$_1$-C$_4$ alkyl, C$_3$-C$_4$ alkenyl, or cyclopropylmethyl;

R$^3$ is hydrogen or C$_1$-C$_4$ alkyl;

n is 1-4;

R$^4$ is hydrogen, C$_1$-C$_4$ alkyl, C$_1$-C$_4$ haloalkyl, C$_1$-C$_4$ alkoxy or phenyl;

R$^5$ and R$^6$ are independently hydrogen, a C$_1$-C$_4$ alkyl, or a C$_5$-C$_8$ cycloalkyl with the proviso that when one or R$^5$ or R$^6$ is a cycloalkyl the other is hydrogen;

R$^7$ is C$_1$-C$_8$ alkyl, trifluoromethyl C$_1$-C$_8$ alkyl substituted with one or two moieties independently selected from C$_1$-C$_3$ alkoxy, halo, hydroxy and C$_1$-C$_3$ alkylthio, aryl, aryl substituted with one or two moieties independently selected from C$_1$-C$_3$ alkoxy, halo, hydroxy, C$_1$-C$_3$ alkylthio, C$_1$-C$_3$ alkyl and trifluoromethyl, aryl (C$_1$-C$_4$ alkyl), aryl (C$_1$-C$_4$ alkyl) substituted with one or two moieties independently selected from C$_1$-C$_3$ alkoxy, halo, hydroxy, C$_1$-C$_3$ alkylthio, C$_1$-C$_3$ alkyl and trifluoromethyl, C$_3$-C$_7$ cycloalkyl-substituted methyl, or C$_3$-C$_7$ cycloalkyl; or a pharmaceutically acceptable salt thereof.

* * * * *

UNITED STATES PATENT AND TRADEMARK OFFICE
CERTIFICATE OF CORRECTION

PATENT NO. : 5,229,410

DATED : July 20, 1993

INVENTOR(S) : Michael E. Flaugh, et al.

It is certified that an error appears in the above-identified patent and that said Letters Patent is hereby corrected as shown below:

Column 40, Line 63, delete "C=C", and insert therefor --C≡C--.

Signed and Sealed this

First Day of November, 1994

Attest:

BRUCE LEHMAN

Attesting Officer

Commissioner of Patents and Trademarks